(12) United States Patent
Kohara et al.

(10) Patent No.: US 11,517,741 B2
(45) Date of Patent: Dec. 6, 2022

(54) ELECTRODES FOR ELECTROPORATION

(71) Applicants: Tokyo Metropolitan Institute of Medical Science, Tokyo (JP); Nepa Gene Co., Ltd., Ichikawa (JP)

(72) Inventors: Michinori Kohara, Tokyo (JP); Yasuhiko Hayakawa, Ichikawa (JP); Kiyoshi Hayakawa, Ichikawa (JP)

(73) Assignees: TOKYO METROPOLITAN INSTITUTE OF MEDICAL SCIENCE, Tokyo (JP); NEPA GENE CO., LTD., Ichikawa (JP)

(*) Notice: Subject to any disclaimer, the term of this patent is extended or adjusted under 35 U.S.C. 154(b) by 1150 days.

(21) Appl. No.: 16/077,979

(22) PCT Filed: Feb. 2, 2017

(86) PCT No.: PCT/JP2017/003733
§ 371 (c)(1),
(2) Date: Aug. 14, 2018

(87) PCT Pub. No.: WO2017/145689
PCT Pub. Date: Aug. 31, 2017

(65) Prior Publication Data
US 2021/0187276 A1 Jun. 24, 2021

(30) Foreign Application Priority Data
Feb. 22, 2016 (JP) .............................. JP2016-030984

(51) Int. Cl.
*A61N 1/04* (2006.01)
(52) U.S. Cl.
CPC .................................. *A61N 1/0424* (2013.01)
(58) Field of Classification Search
CPC ..................................................... A61N 1/0424
See application file for complete search history.

(56) References Cited

U.S. PATENT DOCUMENTS

| | | | |
|---|---|---|---|
| 4,269,174 A | 5/1981 | Adair | |
| 5,439,440 A | 8/1995 | Hofmann | |
| 5,993,434 A | 11/1999 | Dev et al. | |
| 2002/0198485 A1 | 12/2002 | Dev et al. | |

(Continued)

FOREIGN PATENT DOCUMENTS

| CN | 1678369 A | 10/2005 |
|---|---|---|
| JP | H11-506630 | 6/1999 |

(Continued)

OTHER PUBLICATIONS

Extended European Search Report issued for European patent application No. 17756131.3, dated Sep. 30, 2019.

(Continued)

*Primary Examiner* — Joseph M Dietrich
(74) *Attorney, Agent, or Firm* — Westman, Champlin & Koehler, P, A.; Z. Peter Sawicki; Amanda M. Prose

(57) ABSTRACT

An electrode for electroporation comprising a plurality of electrode needles, wherein first polarity electrode needles, an electrode needle holding portion, and a syringe holding portion are provided; two or more first polarity electrode needles project from a bottom surface of a lower structural body of an outer frame support of the electrode needle holding portion toward an electroporation target side; the bottom surface of the lower structural body of the outer frame support is provided with a hole for syringe needle insertion and removal communicating with a syringe holding portion side; the syringe holding portion is provided on a side opposite to the electroporation target side of the electrode needle holding portion; and the syringe holding portion has a path for syringe needle insertion and removal, at least a portion of the path for syringe needle insertion and removal being provided with an electro-conductive portion for a second polarity.

6 Claims, 12 Drawing Sheets

(56) References Cited

U.S. PATENT DOCUMENTS

| | | |
|---|---|---|
| 2003/0009148 A1 | 1/2003 | Hayakawa |
| 2003/0097089 A1 | 5/2003 | Hofmann |
| 2004/0167458 A1 | 8/2004 | Draghia-Akli et al. |
| 2004/0193097 A1 | 9/2004 | Hofmann et al. |
| 2005/0154434 A1 | 7/2005 | Simon et al. |
| 2006/0036210 A1 | 2/2006 | Zhang et al. |
| 2007/0156082 A1 | 7/2007 | Scherman |
| 2008/0058706 A1 | 3/2008 | Zhang et al. |
| 2009/0030364 A1 | 1/2009 | Harmon et al. |
| 2011/0009807 A1 | 1/2011 | Kjeken et al. |
| 2014/0121587 A1 | 5/2014 | Sallberg et al. |
| 2014/0148884 A1 | 5/2014 | Perazzolo Gallo et al. |

FOREIGN PATENT DOCUMENTS

| | | |
|---|---|---|
| JP | 2005-518904 A | 6/2005 |
| JP | 2010-51828 A | 3/2010 |
| JP | 2011-509743 A | 3/2011 |
| JP | 2015-163230 A | 9/2015 |
| KR | 101587930 B1 | 1/2016 |
| WO | 2004/004825 A2 | 1/2004 |
| WO | 2012/137176 A1 | 10/2012 |

OTHER PUBLICATIONS

International Search Report issued for PCT/JP2017/003733 dated Mar. 7, 2017.
Written Opinion of the International Searching Authority issued for PCT/JP2017/003733 dated Mar. 7, 2017.
Notification of Reasons for Refusal issued for JP2017-539032, dated Oct. 5, 2017.
Decision to Grant a Patent issued for JP2017-539032, dated Dec. 25, 2017.
Office Action issued for Chinese patent application No. 201780011616.0 dated Jun. 10, 2021, with English machine translation.

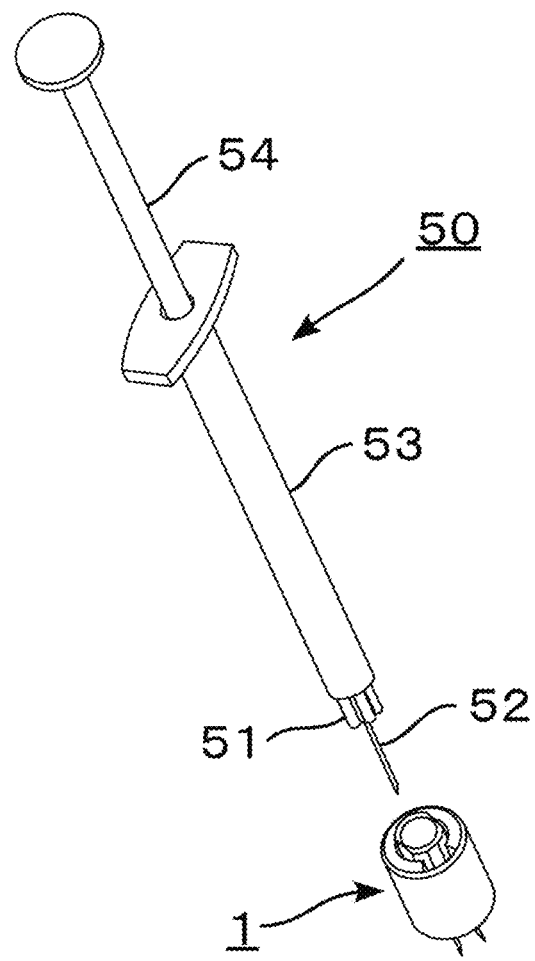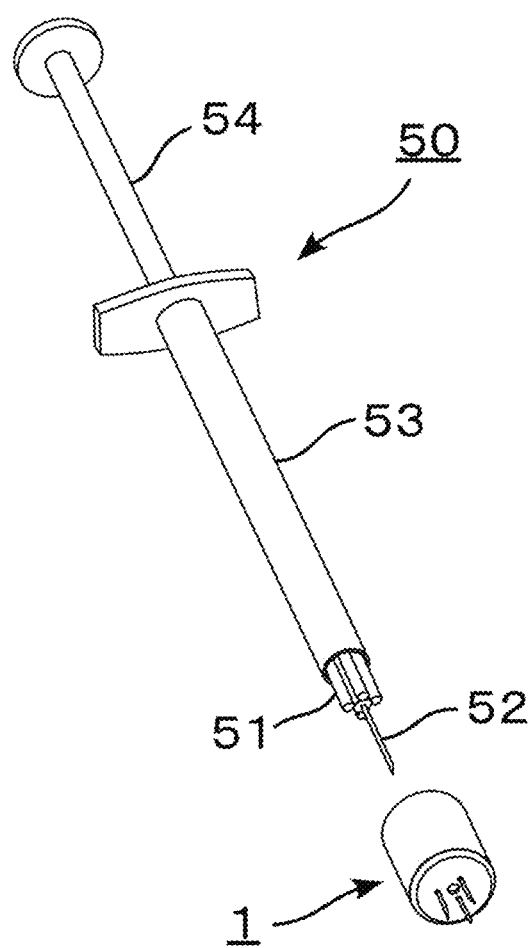

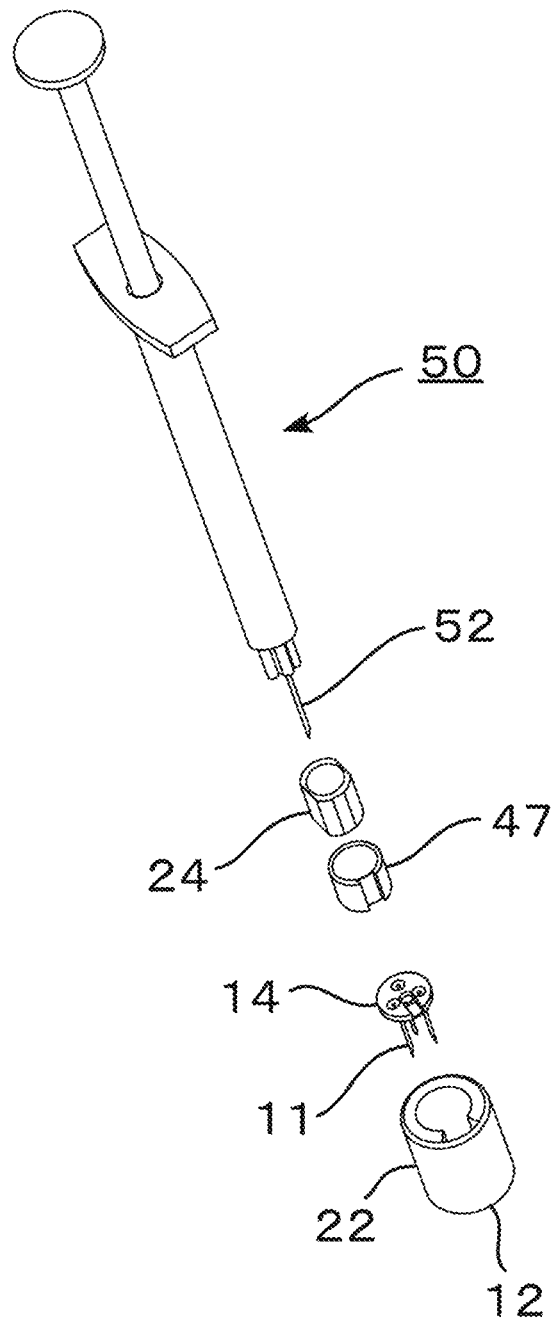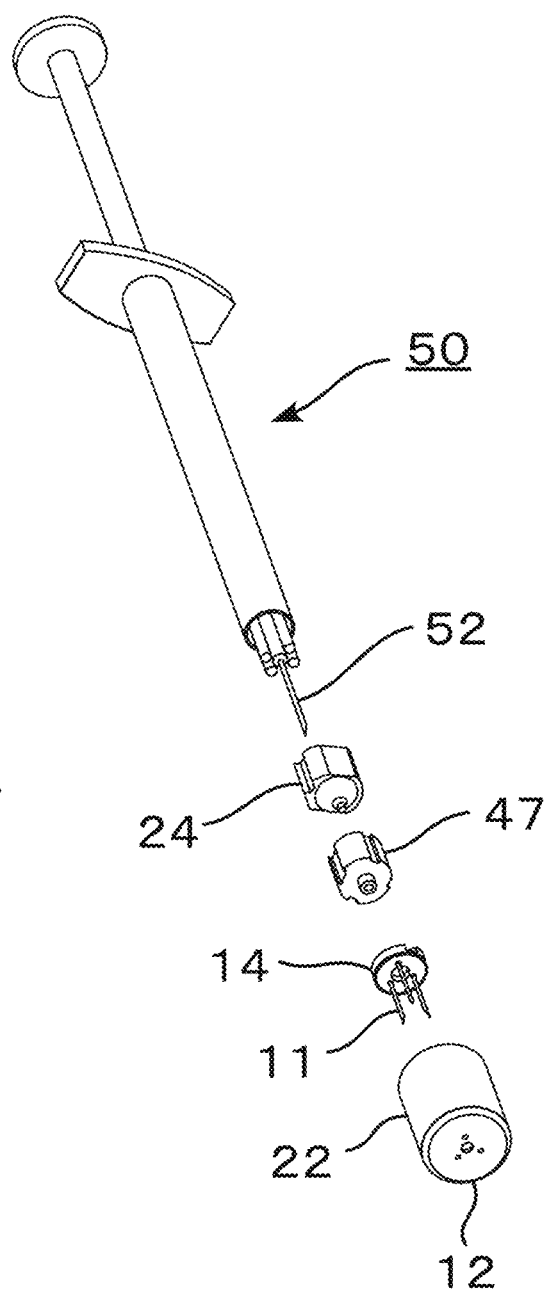

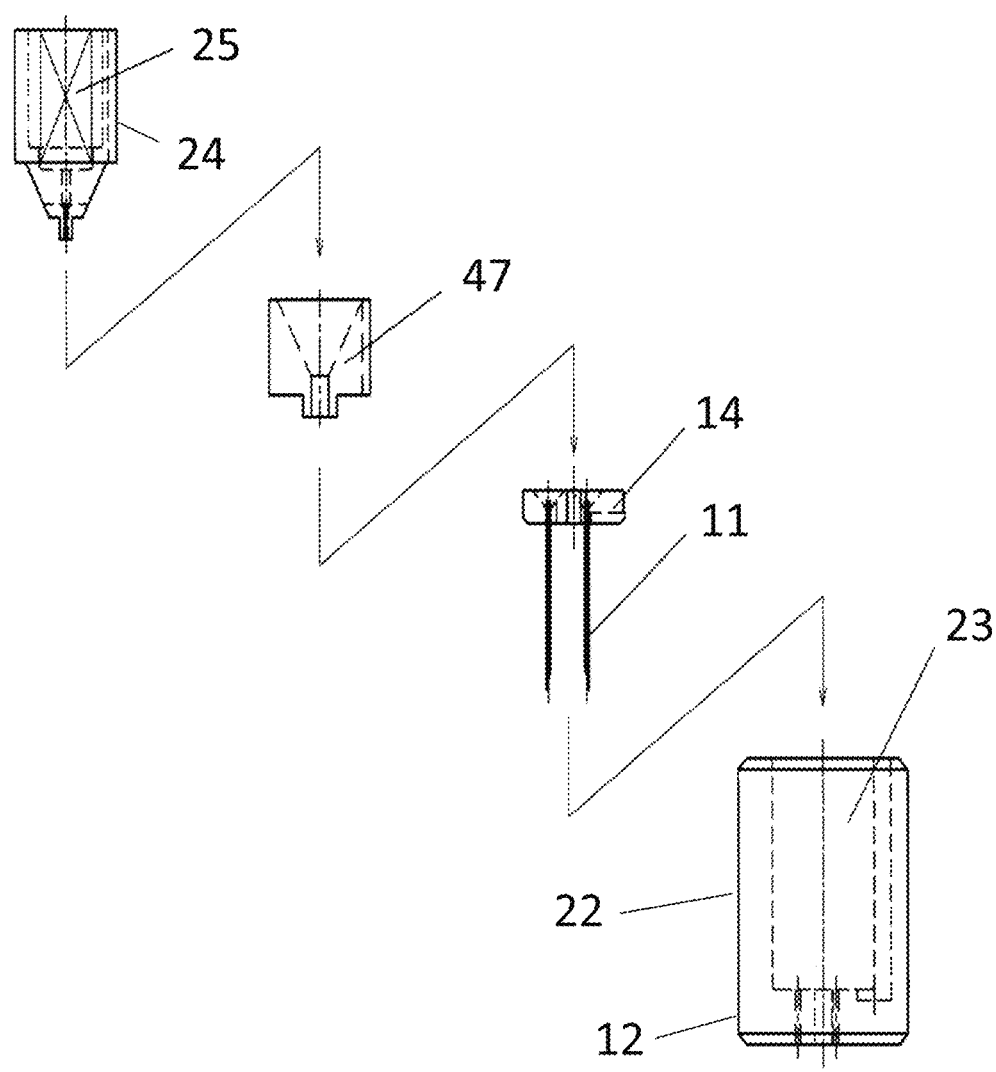

ELECTRODES FOR ELECTROPORATION

CROSS-REFERENCE TO RELATED APPLICATIONS

This application is a Section 371 National Stage Application of International Application No. PCT/JP2017/003733, filed on Feb. 2, 2017, and published as WO2017/145689 A1 on Aug. 31, 2017, which claims priority to and benefits of Japanese Patent Application Serial No. 2016-030984 filed with the Japan Patent Office on Feb. 22, 2016, the entire contents of which are incorporated herein by reference.

TECHNICAL FIELD

The present invention relates to an electrode for electroporation having a plurality of first polarity electrode needles, and more particularly, an electrode for electroporation in which a syringe needle attached can be used as a second polarity electrode needle.

BACKGROUND ART

Electroporation is a method for forming pores in the cell membranes of the target cells by electrical stimulation and achieving easy and efficient introduction of foreign substances into cells. Since electroporation is a method having broad utility as an easy method for introducing nucleic acids, medical substances, and the like, its demand has been increasing in life science research and development and the medical treatment field. However, increase in the usage of electroporation has revealed problems in particular fields. For example, though in vivo electroporation is an important method in the research fields using muscle tissue, skin tissue or the like, it is pointed out that the introduction efficiency of foreign substances is low, and the improvement of introduction efficiency is required.

The main reason for the low introduction efficiency in the in vivo electroporation in muscle tissues, skin tissues or the like is that the experimenters or technicians are required to have special handling skills.

The procedures for performing in vivo electroporation on muscle tissue, skin tissue or the like using general needle electrodes are as follows: (i) a solution containing the substances to be introduced is injected into the target tissue; (ii) the injection site is marked with a marker or the like; (iii) the injection needle is taken out; (iv) using needle electrodes, the needle insertion depth is adjusted; and (v) electric pulses are applied to the target tissue. The entire procedures need to be performed accurately and quickly. In this conventional method, skills are required upon marking the injection site and adjusting the insertion depth, and even if the operator has excellent skills, the experimental results tend to vary. Moreover, since there is a time lag of several tens of seconds to several minutes between the injection of the solution and the application of the electric pulses, there is a fundamental problem that the injected substances are dispersed by the blood flow.

A hand-held electrode device for electroporation treatment having an electrode array with a plurality of electrode needles is disclosed as an electrode device to be used in vivo (Patent Document 1). Since the hand-held electrode device for treatment disclosed in Patent Document 1 has a plurality of electrode needles, it is expected that a larger electric field is generated. However, the improvement in operability in an in vivo situation is not expected because this electrode device requires a series of operations as described above, such as taking out the injection needle after the injection of the substances to be introduced, inserting the electrode needles, and adjusting the needle depth. Therefore, a stable and significant improvement in introduction efficiency in an in vivo situation is not expected when the electrode device of Patent Document 1 is used.

Meanwhile, Patent Document 2 discloses an electrode apparatus for treatment of ailments in which, in an electrode array having a plurality of electrode needles, one or more of the electrodes are cannular. Yet, in Patent Document 2, the portion constituting the electrode array is a part of a hand-held electrode device for treatment of ailments, and the cannular needles are merely a part of the structure integrated with other electrode needles. More specifically, the electrode apparatus of Patent Document 2 is an apparatus in which the multi-electrode needles, the electrode system, cannular needles, the liquid-supplying tube system and the control system are completely integrated. Yet, parts such as the cannular needles and the liquid-supplying tubes attached thereto need to be replaced each time the apparatus is used, and there is a problem in that the assembly of the apparatus or the filling of the sample in the preparation for the experiment cannot be performed quickly or easily. Moreover, if the members for the liquid-supplying system such as the tubular members are reused, the risk of contamination or infection is anticipated.

Therefore, it is hard to admit that the electrode array of the apparatus of Patent Document 2 has a structure that can be stably and conveniently used in research or medical treatment. In this respect, the apparatus of Patent Document 2 presents a new technical problem that has not been found in other prior art.

CITATION LIST

Patent Documents

Patent Document 1: WO2012/137176
Patent Document 2: Japanese Translation of PCT International Application Publication No. H11-506630 JP

SUMMARY OF INVENTION

Technical Problem

The present invention has been achieved in light of the aforementioned circumstances of the conventional techniques, and it is an object thereof to provide a technique that can stably improve the introduction efficiency of foreign substances, and more particularly, a technique for performing in vivo electroporation with quick and easy operations without being affected by the skill of the operator.

Solution to Problem

As a result of intensive study conducted to solve the aforementioned problems, the inventors of the present invention have developed a technique related to an electrode member including first polarity electrode needles, an electrode needle holding portion, and a syringe holding portion, and have achieved the present invention.

Specifically, the inventors have developed a composition of members in which the electrode needle holding portion is a structural body including a lower structural body of an outer frame support and an electro-conductive portion for a first polarity, two or more first polarity electrode needles project from the bottom surface of the lower structural body of the outer frame support toward an electroporation target side, and a bottom surface of the lower structural body of the outer frame support is provided with a hole for syringe needle insertion and removal communicating with a syringe holding portion side.

Also, the inventors have developed a composition of members in which the syringe holding portion for inserting a syringe needle and mounting a syringe is provided on a side opposite to the electroporation target side of the electrode needle holding portion, and the syringe holding portion has a path for syringe needle insertion and removal, at least a portion of the path for syringe needle insertion and removal being provided with an electro-conductive portion for a second polarity made of electro-conductive material.

The inventors of the present invention have found that, by attaching a general syringe having a syringe needle to the syringe holding portion of the electrode structural body having a plurality of first polarity electrode needles, the syringe needle attached can be used as the second polarity electrode needle. That is, the inventors have developed an electrode member having a structure that allows an existing disposable syringe to be attached/detached and have produced an electrode structural body. Then, the inventors have proved its effectiveness by conducting gene introduction experiments.

As a result, the inventors have found that, by using this electrode for electroporation, a series of operations from the injection of a solution containing foreign substances to the application of voltage can be performed stably in a very short time without being affected by the skill of the operator. The inventors have found that, with this technique, the introduction efficiency in in vivo electroporation can be improved. In the method using this electrode structural body, a sample can be installed only by attaching the syringe, and accordingly, a series of operations including the preparatory operations such as the assembly of the electrode apparatus and the filling of the sample can be performed quickly and easily. Moreover, since the sample can be exchanged easily by exchanging the syringe, the risk of contamination and infection can be reduced.

Here, the conventional techniques of Patent Documents 1 and 2 only disclose integrated structures of hand-held electrode devices for treatment, and they neither disclose nor suggest any idea of or any concrete means for realizing a structure with which an existing syringe can be attached/detached and in which the syringe needle is used as the second polarity electrode needle.

The present invention specifically relates to aspects of the invention described below.

[1] An electrode for electroporation including a plurality of electrode needles, wherein (A) first polarity electrode needles, an electrode needle holding portion, and a syringe holding portion are provided;

(B) the electrode needle holding portion is a structural body including a lower structural body of an outer frame support and an electro-conductive portion for a first polarity, a bottom surface of the lower structural body of the outer frame support being provided with a hole for syringe needle insertion and removal communicating with a syringe holding portion side;

(C) two or more first polarity electrode needles project from the bottom surface of the lower structural body of the outer frame support toward an electroporation target side; and (D) (d-1) the syringe holding portion for inserting a syringe needle and mounting a syringe is provided on a side opposite to the electroporation target side of the electrode needle holding portion, and (d-2) the syringe holding portion has a path for syringe needle insertion and removal, at least a portion of the path for syringe needle insertion and removal being provided with an electro-conductive portion for a second polarity made of electro-conductive material.

[2] The electrode for electroporation according to aspect 1, which is an electrode member in which, when the syringe is attached to the syringe holding portion and the syringe needle is brought into contact with the electro-conductive portion for the second polarity, the syringe needle projecting from the hole for syringe needle insertion and removal can be used as a second polarity electrode needle.

[3] The electrode for electroporation according to aspect 1 or 2, wherein, when viewed from the bottom of the lower structural body of the outer frame support, the hole for syringe needle insertion and removal is disposed on a straight line or a substantially straight line connecting tips of the first polarity electrode needles or inside a polygon whose apexes are the tips of the first polarity electrode needles.

[4] The electrode for electroporation according to any one of aspects 1 to 3, wherein at least a portion of the electro-conductive portion for the second polarity in the path for syringe needle insertion and removal has a straight-tubular structure made of electro-conductive material and has an inner diameter or an inner width that ensures contact with the syringe needle inserted.

[5] The electrode for electroporation according to any one of aspects 1 to 4, wherein the first polarity electrode needles penetrate the lower structural body of the outer frame support of the electrode needle holding portion and are connected to the electro-conductive portion for the first polarity.

[6] The electrode for electroporation according to any one of aspects 1 to 5, wherein (E) the first polarity electrode needles, together with a part of or the entire lower structural body of the outer frame support, can be attached and detached due to (e-1) a structure in which the first polarity electrode needles can be attached and detached at a connecting portion between the first polarity electrode needles and the electro-conductive portion for the first polarity, or (e-2) a structure in which a connecting portion that can detach the electro-conductive portion for the first polarity is provided.

[7] The electrode for electroporation according to any one of aspects 1 to 6, wherein angles at which the first polarity electrode needles project are perpendicular to and/or substantially perpendicular to the bottom surface of the lower structural body of the outer frame support.

[8] The electrode for electroporation according to any one of aspects 1 to 7, wherein the number of the first polarity electrode needles is three or more.

[9] The electrode for electroporation according to any one of aspects 1 to 8, wherein the first polarity electrode needles are located within a range of 0.5 to 10 mm from a center of the hole for syringe needle insertion and removal when viewed from the bottom of the lower structural body of the outer frame support.

[10] The electrode for electroporation according to any one of aspects 1 to 9, wherein the first polarity electrode needles are arranged at equal intervals or substantially equal intervals on concentric circles or substantially concentric circles around the hole for syringe needle insertion and removal when viewed from the bottom of the lower structural body of the outer frame support.

[11] The electrode for electroporation according to any one of aspects 1 to 10, wherein the first polarity electrode needles are fixed electrode needles, and a length of their portion projecting from the bottom surface of the outer frame support of the electrode needle holding portion is within a range of 1 to 10 mm.

[12] An electrode for electroporation, wherein the syringe is attached to the syringe holding portion of the electrode for electroporation according to any one of aspects 1 to 11; the syringe needle projects from the hole for syringe needle insertion and removal; and the projecting syringe needle functions as the second polarity electrode needle, as the syringe needle is brought into contact with the electro-conductive portion for the second polarity.

[13] The electrode for electroporation according to aspect 12, wherein a length of a projecting portion of the syringe needle, which serves as the second polarity electrode needle, from the hole for syringe needle insertion and removal falls within a range of −4 to +2 mm compared with an average length of projecting portions of the first polarity electrode needles from the bottom surface of the lower structural body of the outer frame support.

[14] A kit for assembling the electrode for electroporation according to any one of aspects 1 to 13, including members of the first polarity electrode needles, the electrode needle holding portion, and the syringe holding portion.

Advantageous Effects of Invention

The present invention provides a technique that can stably improve the introduction efficiency of foreign substances, and more particularly, a technique for performing in vivo electroporation with quick and easy operations without being affected by the skill of the operator. For example, the present invention can realize efficient in vivo electroporation in muscle tissue or skin tissue, in which conventional techniques could only achieve low gene introduction efficiency.

BRIEF DESCRIPTION OF DRAWINGS

FIGS. 1A and 1B illustrate perspective views of the electrode for electroporation according to one example of the present invention. The syringe in this figure is illustrated as a member before being attached to the electrode for electroporation according to the present invention. FIG. 1A is a top perspective view. FIG. 1B is a bottom perspective view.

FIGS. 2A and 2B illustrate exploded perspective views showing the main components of the electrode for electroporation according to one example of the present invention. The syringe in this figure is illustrated as a member before being attached to the electrode for electroporation according to the present invention. FIG. 2A is a top perspective view. FIG. 2B is a bottom perspective view.

FIG. 3 is an exploded longitudinal cross-sectional view showing the main components of the electrode for electroporation according to one example of the present invention.

FIG. 12A is a bottom view image taken from the lower structural body side of the outer frame support. FIG. 12B is a top view image taken from the syringe barrel end attachment portion side.

FIG. 13A is a side view image. FIG. 13B is a side view image with a syringe attached.

FIG. 14A: 0 μg of DNA introduced. FIG. 14B: 25 μg of DNA introduced. FIG. 14C: 50 μg of DNA introduced. FIG. 14D: 75 μg of DNA introduced. FIG. 14E: 100 μg of DNA introduced.

DESCRIPTION OF EMBODIMENTS

Figure 4:
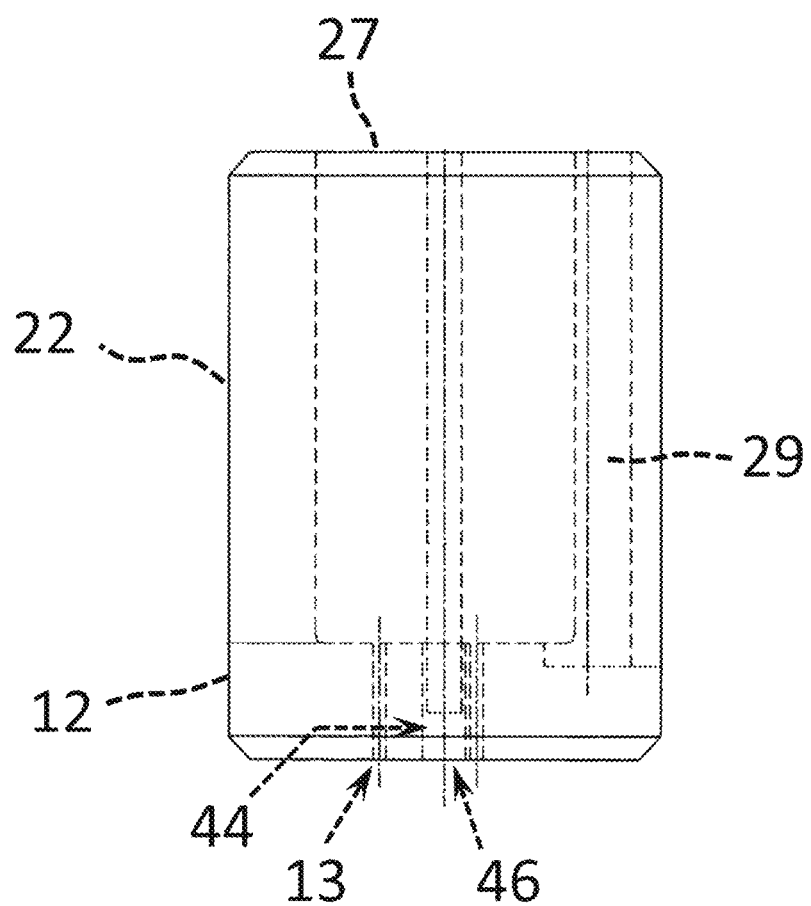
FIG. 4 is a longitudinal cross-sectional view of the lower structural body of the outer frame support and the outer structural body of the syringe barrel end attachment portion (the upper structural body of the outer frame support) of the electrode for electroporation according to one example of the present invention.
Figure 5:
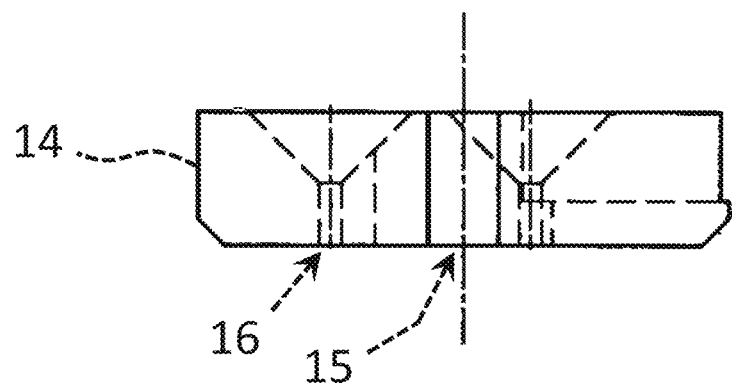
FIG. 5 is a longitudinal cross-sectional view of the electro-conductive portion for the first polarity of the electrode for electroporation according to one example of the present invention.
Figure 6:
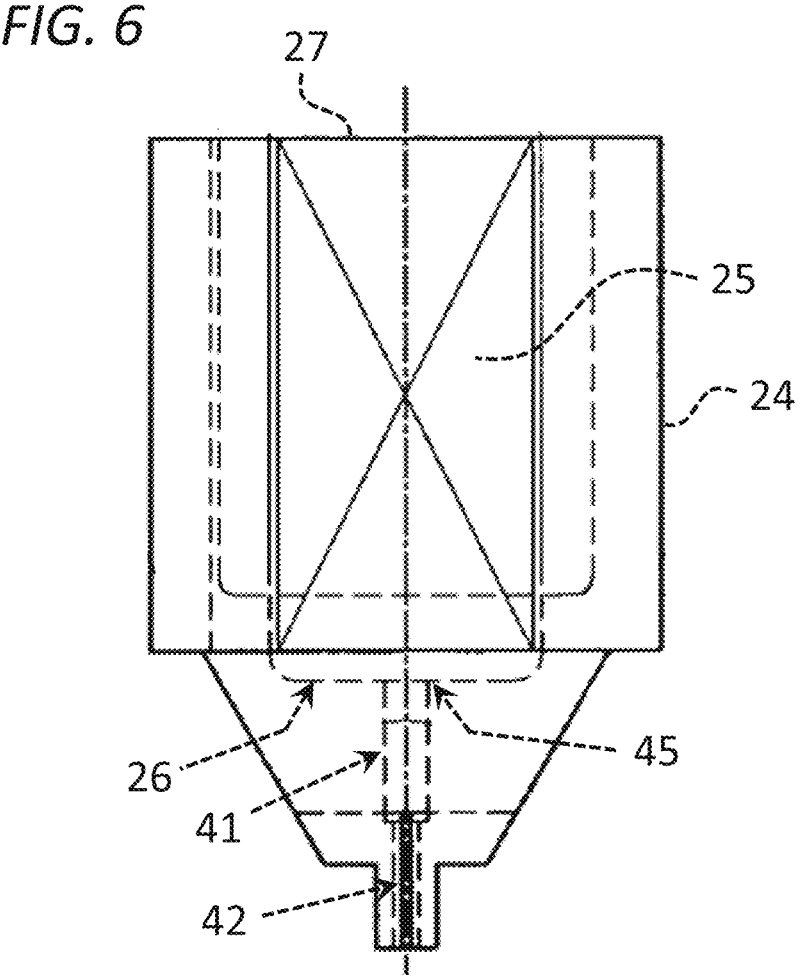
FIG. 6 is a longitudinal cross-sectional view of the inner structural body of the syringe barrel end attachment portion and a part of the path for syringe needle insertion and removal of the electrode for electroporation according to one example of the present invention.
Figure 7:
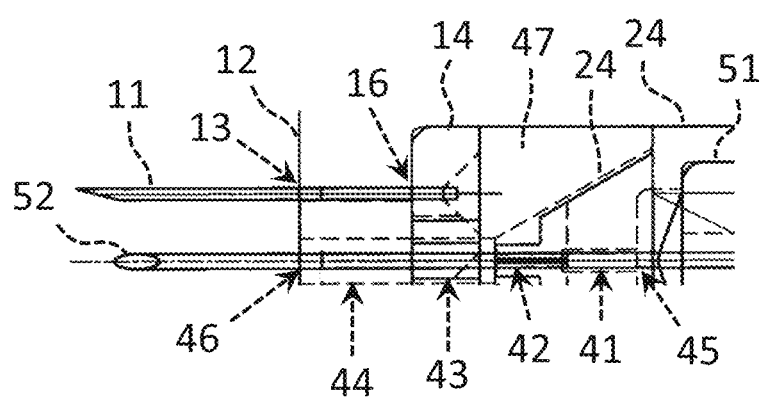
FIG. 7 is a longitudinal cross-sectional view of the path for syringe needle insertion and removal and its surrounding portion with a syringe attached in the electrode for electroporation according to one example of the present invention. The electroporation target side is on the left side of the figure.
Figure 8:
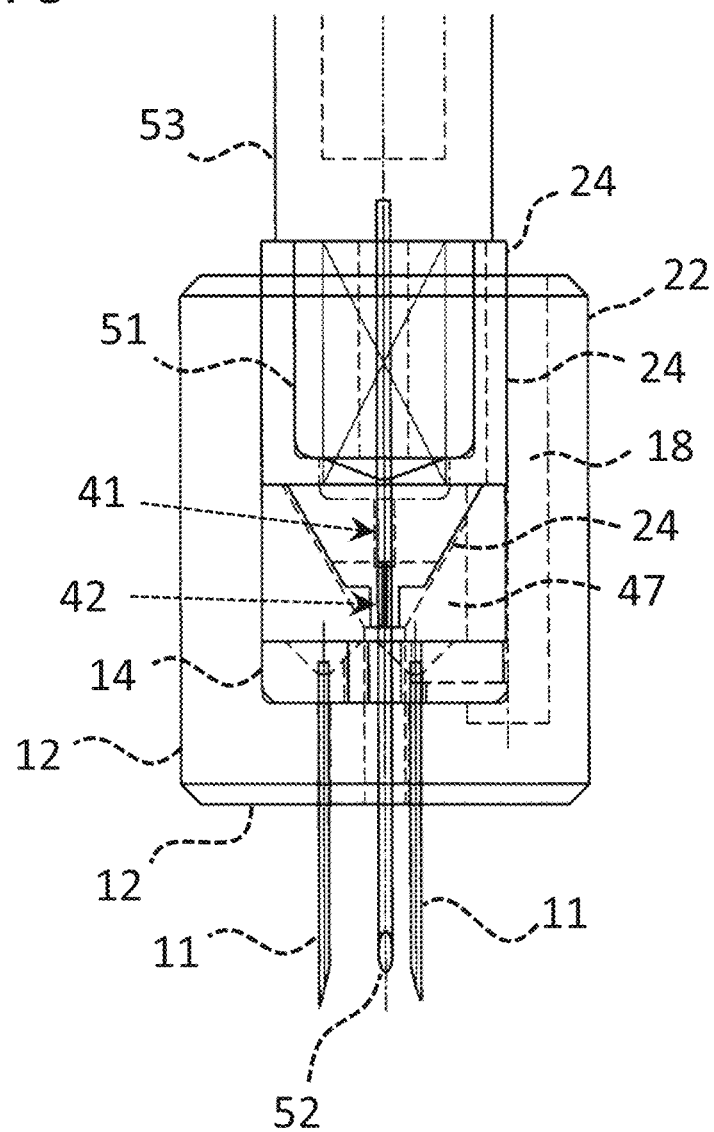
FIG. 8 is a longitudinal cross-sectional view of the electrode for electroporation with a syringe attached according to one example of the present invention.
Figure 9:
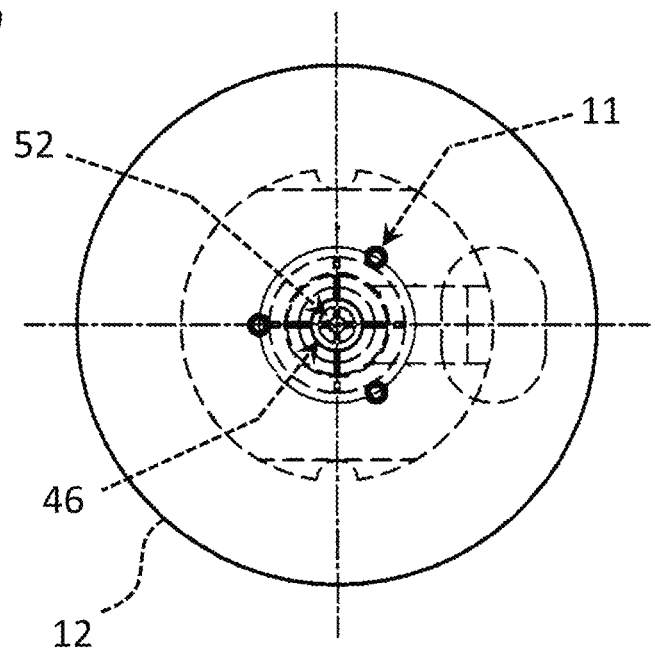
FIG. 9 is a bottom plan view of the electrode for electroporation with a syringe attached in one example of the present invention.
Figure 10:
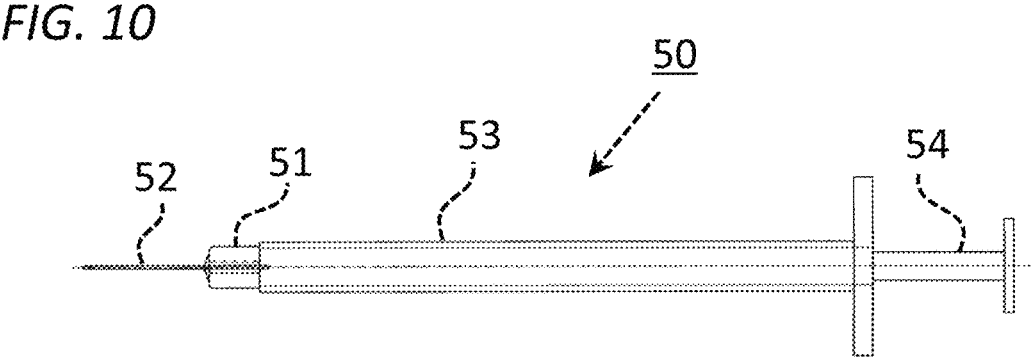
FIG. 10 is a side view of a syringe that can be attached to the electrode for electroporation according to one example of the present invention.

The present application claims priority based on Japanese Patent Application No. 2016-030984, which was filed in Japan by the applicants of the present invention, and which is hereby incorporated by reference in its entirety.

Hereinafter, embodiments of the present invention will be described in detail. The reference numerals in the following description refer to those used in the drawings.

Terminology

The term "electroporation" as used herein is a method in which electric pulses are applied to cells, small pores that allows the passage of foreign substances are formed temporarily in the cell membranes, and foreign substances are introduced into target cells. It is a versatile method for introducing foreign substances and can be applied to various species, tissues, cells, and the like.

The term "in vivo" as used herein refers to inside a living body. It is a term as opposed to the term "in vitro", which refers to inside a laboratory vessel.

The term "foreign substances to be introduced" (hereinafter, also referred to "foreign substances", "substances to be introduced" or the like) refers to the substances to be introduced into the cells from outside by electroporation. It encompasses any substances that can be introduced by electroporation. Examples of the foreign substances to be introduced are various kinds of biologically active substances that cannot or can hardly pass through the cell membrane under normal conditions, drugs, therapeutic medicines, nucleic acid substances, peptides and proteins.

Examples of nucleic acid substances include DNA and RNA. DNA having a desired sequence can be appropriately selected to be introduced into the target cell. DNA constructed for a specific purpose can be used, and its examples include, but are not limited to, a full-length sequence (e.g. a cDNA sequence, and a genome sequence), a partial sequence, a regulatory region, a spacer region, and a mutated sequence. Virus DNA, plasmid DNA, oligonucleotides (e.g. antisense oligonucleotides, and aptamers) and peptide nucleic acids are also included. Examples of RNA include, but are not limited to, mRNA and siRNA.

With regard to the terms "fist polarity" and "second polarity" as used herein, when one polarity (e.g. positive polarity) of the voltage applied is regarded as the first polarity, the other polarity (negative polarity in this case) is regarded as the second polarity. Any polarity can be selected for the first and the second polarities.

The term "syringe" as used herein indicates the entire syringe 50 obtained by assembling a syringe barrel 53, a plunger 54 and a needle 52 (syringe needle).

The "upper side" of the electrode for electroporation as used herein indicates the syringe holding portion side unless otherwise specified. The "lower side" of the electrode for electroporation as used herein indicates the lower structural body side of the outer frame support of the electrode needle holding portion unless otherwise specified. While the terms regarding the directions, such as the "upper side", "lower side", "upper portion", "lower portion", "bottom portion", "horizontal" and "vertical" are used herein to explain the structure of the electrode, they do not limit the actual direction of the electrode when it is used.

The expression of figures, shapes, angles or the like modified with the word "substantially" herein indicates that some changes can be added to the figures or the like.

For example, when a word indicating an angle or a direction is modified with the word "substantially" in the present description, the angle or the direction can have an inclination to an extent that practically does not cause any problems.

Also, when the figure, shape, arrangement or the like modified with the word "substantially" is circular or the like, it encompasses deformed shapes of a circle such as a shape with its circumference distorted to some extent, an ellipse and an oval. When a polygonal shape or the like is referred to, it encompasses deformed shapes of a polygonal shape such as those with round corners and those with its periphery distorted to some extent. Similarly, when a lattice pattern or the like is referred to, deformation of the shapes formed by its components is permissible. Also, a straight line encompasses a distorted line and a curve with a low curvature. The same definition can be applied to the entire shape and the cross-sectional shape of a three-dimensional shape.

1. Electrode for Electroporation Including a Plurality of Electrode Needles

The present invention relates to an electrode for electroporation including a plurality of electrode needles, provided with first polarity electrode needles 11, an electrode needle holding portion 10, and a syringe holding portion 20. Particularly, it relates to the electrode for electroporation having a plurality of first polarity electrode needles, in which a syringe needle 52 can serve as a second polarity electrode needle when a syringe 50 is attached.

The following table summarizes the structures and their main components in the electrode for electroporation 1 according to the present invention. Though Table 1 summarizes the structures and their main components, it is not intended to show the requisite members in the present invention. Therefore, the technical scope of the present invention is not limited to an aspect including all the members described in Table 1.

TABLE 1

| Main components of the electrode for electroporation 1 according to the present invention | | |
|---|---|---|
| Structures related to the first polarity | Electrode needle holding portion 10 | First polarity electrode needles 11 Lower structural body 12 of the outer frame support Electro-conductive portion 14 for the first polarity |
| Structures related to the second polarity | Syringe holding portion 20 | Syringe barrel end attachment portion 21 Outer structural body 22 (Upper structural body of the outer frame support) Inner structural body 24 Path for syringe needle insertion and removal 40 Electro-conductive portion 42 for the second polarity |

[Structure Related to the First Polarity]

In the electrode for electroporation 1 according to the present invention, the structure related to the first polarity includes the first polarity electrode needles 11, the electrode needle holding portion 10, and the like. In addition, the structure related to the first polarity may include wiring, conducting wires and/or power cables for connecting to the power source, and supporting members for reinforcing the outer frame support.

[First Polarity Electrode Needles]

In the electrode for electroporation 1 according to the present invention, the first polarity electrode needles 11 project from the bottom surface of the lower structural body of the outer frame support toward an electroporation target side.

The term "first polarity electrode needles" 11 as used herein indicate needle-like electrodes having one of the polarities of the voltage applied.

The first polarity electrode needles 11 are preferably made of electro-conductive material. They can be made of any material that can be generally used as an electrode. Preferable examples are stainless steel, platinum, steel, copper, iron, titanium alloy, aluminum alloy and carbon.

Metallic material which is resistant to rust and whose impact on the body is not concerned is especially preferable as the material of the first polarity electrode needles 11. Preferable examples thereof are stainless steel, platinum and titanium alloy.

The first polarity electrode needles 11 can have any needle or needle-like shapes having a sharp tip and suitable for piercing into living tissue. A shape having an angle or a curvature, such as a bent or curved shape, is also acceptable as long as it has a sharp tip.

A branched shape, a shape branched into a plurality of needles toward the tip, a shape in which a plurality of needles are merged at the tip, and the like, can also be employed for the first polarity electrode needles 11. It is also possible to employ a structure in which the base sides of the portions of the electrode needles projecting from the bottom surface of the lower structural body 12 of the outer frame support are covered by insulating members. It is also possible to employ a structure in which a planar structure, a substantially planar structure, an annular structure or the like which is horizontal to or forms a shallow angle with respect to the bottom surface of the lower structural body of the outer frame support is provided at the base side of the portions of the electrode needles projecting from the bottom surface of the lower structural body 12 of the outer frame support, and in which one needle or needle-like shape or two or more needle or needle-like shapes project from this structure.

A preferable example of the shape of the first polarity electrode needles 11 is a shape including a sharp straight-rod or straight-tubular needle shape. A more preferable example is a sharp straight-rod or straight-tubular shape used in medical treatment or acupuncture. Examples thereof are needles having a hypodermic needle shape, a hollow needle shape, an injection needle shape, an acupuncture needle shape, or an acute-angled conical shape. The examples of the cross-sectional shape of the needles are a circular shape, a substantially circular shape, an elliptical shape, an oval shape, an annular shape and a polygonal annular shape, and a circular shape and a substantially circular shape are especially preferable.

It is preferable that a first polarity electrode needle 11 has a cross section with an outer diameter suitable for piercing into living tissue, and the example of the outer diameter is 0.5 mm or less, preferably 0.4 mm or less, more preferably 0.35 mm or less, more preferably 0.33 mm or less, more preferably 0.30 mm or less, more preferably 0.28 mm or less, and even more preferably 0.26 mm or less. There is no particular lower limit on the outer diameter if the strength of the needle can be ensured, and examples thereof are 0.1 mm or more, and preferably 0.15 mm or more.

In a preferable mode of the electrode for electroporation 1 according to the present invention, the first polarity electrode needles 11 are provided as fixed electrode needles.

Here, in one possible mode of the present invention, a mechanism for freely adjusting the length of the first polarity electrode needles 11 can be provided. However, one of the technical problem to be solved in the present invention is to realize simple operability. Moreover, when the production efficiency is taken into consideration, the first polarity electrode needles are preferably provided as fixed electrode needles.

With regard to the length of the first polarity electrode needles 11, the length of the projecting portions of the first polarity electrode needles 11 from the bottom surface of the lower structural body 12 of the outer frame support of the electrode needle holding portion is preferably 1 mm or more, preferably 2 mm or more, more preferably 3 mm or more, and even more preferably 4 mm or more. The upper limit thereof is 10 mm or less, preferably 8 mm or less, more preferably 6 mm or less, and even more preferably 5 mm or less. That is, it is desirable that the length is within a range of 1 to 10 mm, preferably 2 to 8 mm, more preferably 3 to 6 mm, and even more preferably 4 to 5 mm.

Each first polarity electrode needle 11 has a length that falls within a range of −2 to +2 mm, preferably −1 to +1 mm, more preferably −0.5 to +0.5 mm, and even more preferably −0.2 to +0.2 mm compared with the average needle length of the projecting portions of the first polarity electrode needles 11 from the bottom surface of the lower structural body 12 of the outer frame support of the electrode needle holding portion. Most preferably, all of the portions of the first polarity electrode needles 11 projecting from the bottom surface of the lower structural body 12 of the outer frame support of the electrode needle holding portion have the same length.

Here, the base portions of the first polarity electrode needles 11 are buried inside the lower structural body 12 of the outer frame support of the electrode needle holding portion and are not included in the needle length mentioned above. Therefore, there is no particular limitation on the needle length of these buried portions.

The needle length of the first polarity electrode needles 11 preferably indicates the length of the straight-rod or straight-tubular portion of the portion protruding from the bottom surface.

When the electrode for electroporation 1 according to the present invention is provided with fixed electrodes having the predetermined needle length as mentioned above, it becomes unnecessary to perform complex operations for adjusting the needle depth or the like upon inserting the needles into the muscle or the skin. The fixed electrode needle length within the aforementioned range can realize the appropriate insertion depth when performing electroporation on the muscle or the skin.

Therefore, with the electrode for electroporation according to the present invention, the electrode needles can be inserted to a depth suitable for electroporation only with a simple operation of fully inserting the electrode needles to the bottom.

In the electrode for electroporation 1 according to the present invention, when viewed from the bottom of the lower structural body 12 of the outer frame support, the hole for syringe needle insertion and removal 46 is disposed on a straight line or a substantially straight line connecting the tips of the first polarity electrode needles 11 or inside the polygon whose apexes are the tips of the first polarity electrode needles 11. It is also preferable that the first polarity electrode needles 11 are arranged so that the hole for syringe needle insertion and removal 46 may be located on a straight line or a substantially straight line connecting the base portions of the first polarity electrode needles 11 or inside the polygon whose apexes are the base portions of the first polarity electrode needles 11 when viewed from the bottom of the lower structural body 12 of the outer frame support.

The first polarity electrode needles 11 are preferably located at a position within a range of 0.5 to 10 mm, preferably 0.5 to 5 mm, more preferably 0.75 to 4 mm, more preferably 1 to 3 mm, and even more preferably 1 to 2 mm from the center of the hole for syringe needle insertion and removal 46 when viewed from the bottom of the lower structural body 12 of the outer frame support of the electrode needle holding portion. This range preferably indicates the range of the distance between the tip of the electrode needle and the hole for syringe needle insertion and removal in the bottom view.

It is preferable that the distance between the first polarity electrode needles 11 and the hole for syringe needle insertion and removal is within the aforementioned range, because high electric field strength (V/cm) can be achieved even when the applied voltage is low, and the damage to the tissue or cells can be reduced. It is not preferable if the distance is too longer than the aforementioned range, because it becomes necessary to apply a high voltage to obtain the required strength of the electric field. Moreover, it is not preferable if the distance is too shorter than the aforementioned range, because the area to be subjected to electroporation becomes too small, and it becomes difficult to introduce genes to a sufficient area.

The first polarity electrode needles 11 are preferably arranged on concentric circles or substantially concentric circles around the hole for syringe needle insertion and removal 46 when viewed from the bottom of the lower structural body 12 of the outer frame support of the electrode needle holding portion. The first polarity electrode needles 11 are preferably arranged at equal intervals or substantially equal intervals.

Specifically, when the number of the needles constituting the first polarity electrode needles is two, they are preferably disposed on a straight line or substantially straight line passing through the hole for syringe needle insertion and removal 46, at equal intervals or substantially equal intervals from the hole for syringe needle insertion and removal, when viewed from the bottom of the lower structural body 12 of the outer frame support of the electrode needle holding portion. When the number of the needles constituting the first polarity electrode needles is three or more, they are preferably disposed so that the polygon whose apexes are these electrode needles may form a regular polygon or a substantially regular polygon when viewed from the bottom of the lower structural body 12 of the outer frame support of the electrode needle holding portion. These positions preferably indicate the positions of the tips of the electrode needles and the hole for syringe needle insertion and removal in the bottom view.

In the electrode for electroporation 1 according to the present invention, it is preferable that the distances between the syringe needle 52, which is the second polarity electrode needle, (or the hole for syringe needle insertion and removal 46) and each of the first polarity electrode needles 11 are closer to equal, because the more nearly equal the distances, the more uniform electric field can be generated. Moreover, in the electrode for electroporation 1 according to the present invention, it is preferable that the intervals between the first polarity electrode needles 11 are closer to equal, because the more nearly equal the intervals, the more uniform electric field can be generated.

In the electrode for electroporation 1 according to the present invention, an example of the number of the first polarity electrode needles 11 projecting from the bottom surface of the lower structural body 12 of the outer frame support is two or more, and it is more preferably three or more. It is preferable to provide three or more first polarity electrode needles 11, because electric field can be generated in the polygonal area formed by the first polarity electrode needles 11, and the area to be subjected to electroporation can become larger.

The appropriate number of the first polarity electrode needles 11 is 2 to 8, preferably 3 to 7, more preferably 3 to 6, more preferably 3 to 5, and even more preferably 3 to 4. In principle, it is preferable that the number of the first polarity electrode needles 11 is larger, because the larger the number, the larger the area to be subjected to electroporation. However, it is not preferable to increase the number of electrodes beyond a predetermined level, because the problems in the production efficiency and costs exceed the benefits of increasing the number of the electrodes, and moreover, the increased electrode needles may cause pain in research subjects.

With regard to the angle at which the first polarity electrode needles 11 project from the bottom surface of the lower structural body 12 of the outer frame support of the electrode needle holding portion, it is preferable that the first polarity electrode needles 11 are disposed and fixed perpendicular to or substantially perpendicular to the bottom surface of the lower structural body of the outer frame support. The term "substantially perpendicular" as used herein preferably indicates angles within a range of 90±10°, preferably 90±5°, and more preferably 90±2° with respect to the bottom surface of the lower structural body 12 of the outer frame support. It is not preferable if the angles at which the first polarity electrode needles 11 project are not within an appropriate range, because it becomes hard for the needles to be inserted into or removed from living tissue.

Most preferably, the first polarity electrode needles are disposed and fixed perpendicular to the bottom surface of the lower structural body of the outer frame support.

When the portions of the first polarity electrode needles 11 projecting from the bottom surface have angled shapes, it is preferable that the angles of the straight-rod-shaped or straight-tubular-shaped portions at the tip portions with respect to the bottom surface of the lower structural body of the outer frame support are within the range mentioned above.

[Electrode Needle Holding Portion]

The electrode for electroporation 1 according to the present invention has an electrode needle holding portion 10 provided with structure or means for physically supporting the first polarity electrode needles 11 and supplying voltage to the first polarity electrode needles 11. With the structure of the electrode needle holding portion 10 in the present invention, the shapes such as the arrangement and structure of the electrodes can be physically maintained, and such functions as supplying voltage to the electrodes can be exhibited. The electrode needle holding portion 10 is a member that has, as its component members, the lower structural body 12 of the outer frame support and the electro-conductive portion 14 for the first polarity as described below.

Lower Structural Body of the Outer Frame Support

The members of the electrode needle holding portion 10 include the lower structural body of the outer frame support (12: the lower structure of the housing in the Examples) for supporting the first polarity electrode needles 11. The lower structural body 12 of the outer frame support is a housing member provided with structure and functions for fixing the first polarity electrode needles 11. The term "lower" as used herein indicates the lower part of the entire structure of the electrode 1 of the present invention and can be used even in an embodiment in which the electrode 1 does not have the upper structural body of the outer frame support.

The lower structural body 12 of the outer frame support has a shape forming the bottom surface facing the electroporation target. Preferable examples of the shape of the bottom surface of the lower structural body 12 of the outer frame support are a flat planar shape and a substantially flat planar shape, and other various shapes, such as a shape having a curved surface or a three-dimensional shape, can also be employed. For example, it is possible to employ a dome shape, a conical shape, a polygonal pyramid shape, a truncated conical shape, a truncated polygonal pyramid shape, a quadrangular pillar shape, a polygonal pillar shape, or a stepped pyramid shape. A shape substantially similar to the aforementioned shapes can also be employed. It is possible to employ not only a shape protruded toward the electroporation target side but also a concave shape. When a three-dimensional shape is employed for the bottom surface, a shape with a low curvature or gradient is preferable.

Most preferably, the bottom surface of the lower structural body 12 of the outer frame support has a flat planar shape so that the voltage can be applied uniformly to the target of electroporation.

With regard to the entire shape of the lower structural body 12 of the outer frame support, it is preferably a structural body which has the above-mentioned bottom surface shape and has a certain thickness for physically supporting the first polarity electrode needles. It preferably has a container-like shape whose upper portion has an upper or inner space for connecting to and fixing the electro-conductive portion for the first polarity. For example, a box shape or a tubular shape is preferable.

Though any shape can be employed without limitation, its cross-sectional shape is preferably circular or substantially circular because the lower structural body 12 of the outer frame support is arranged consecutively with or connected to the syringe holding portion 20.

The bottom surface portion of the lower structural body 12 of the outer frame support can have any thickness capable of physically supporting the first polarity electrode needles, and examples thereof are 0.2 to 10 mm, preferably 0.5 to 5 mm, and more preferably about 0.7 to 2 mm With regard to the width of the lower structural body 12 of the outer frame support, examples of the outer width in bottom view are 4 to 50 mm, preferably 6 to 30 mm, and more preferably about 7 to 20 mm.

The lower structural body 12 of the outer frame support preferably has a shape provided with the first polarity electrode through holes 13, to which the first polarity electrode needles 11 are attached and fixed, and the hole for syringe needle insertion and removal 46, through which the syringe needle 52, or the second polarity electrode needle, can be inserted or removed.

A hole through which the syringe needle 52 can be smoothly inserted or removed can be employed for the hole for syringe needle insertion and removal 46, and for example, a hole with its inner diameter or inner width of 0.1 to 4 mm, preferably 0.3 to 3 mm, more preferably 0.4 to 2 mm, and more preferably about 0.5 to 1.5 mm can be employed.

The first polarity electrode through holes 13 and the hole for syringe needle insertion and removal 46 are preferably formed at positions that can dispose the first polarity electrode needles 11 in an arrangement described in paragraphs above. That is, the bottom surface of the lower structural body 12 of the outer frame support preferably has a structure in which the hole for syringe needle insertion and removal 46, which communicates with the syringe holding portion side, is positioned on a straight line or a substantially straight line connecting the first polarity electrode through holes 13 or inside the polygon whose apexes are the first polarity electrode through holes 13.

The upper portion of the lower structural body 12 of the outer frame support preferably has a structure suitable for attaching the electro-conductive portion 14 for the first polarity. It preferably has a structure or a means suitable for fitting, engagement, connection or the like so that the electro-conductive portion 14 for the first polarity can be fitted inside.

The lower structural body 12 of the outer frame support is preferably made of an electrically insulating member or electrically insulating material. At least the portions of the lower structural body 12 of the outer frame support around the first polarity electrode through holes 13 and around the hole for syringe needle insertion and removal 46 are made of electrically insulating material. Preferably, the entire lower structural body 12 of the outer frame support is practically made of insulating material. The material preferably has durability as a housing. More preferably, the material has heat resistance.

The electrically insulating material can be made of any material having hardness and durability, and examples thereof are resin, glass and ore. Preferable examples are polystyrene, polyethylene terephthalate (PET), polypropylene, polycarbonate, polymethyl methacrylate, polymethyl pentene, ABS resins, acrylic resins, fluorocarbon resins (e.g. PTFE, PFA and FEP), polyether ether ketone (PEEK) resins, polyimide resins and ceramic (e.g. alumina and aluminum nitride).

The lower structural body 12 of the outer frame support is a member arranged continuously with and/or being connected to the syringe barrel end attachment portion 21, which is a member of the syringe holding portion 20. The lower structural body 12 of the outer frame support and the outer part of the syringe barrel end attachment portion (22: upper structural body of the outer frame support) can be provided as an integrated continuous member depending on the requirements of particular embodiments.

In another embodiment, the lower structural body 12 of the outer frame support can be attached and detached at a connecting portion with the syringe holding portion 20. In this embodiment, the entire lower structural body 12 of the outer frame support, together with the first polarity electrode needles 11, can be attached to and detached from the main body of the electrode.

In still another embodiment, the lower structural body 12 of the outer frame support can be separated into upper and lower structures. In this embodiment, a part of the lower structural body 12 of the outer frame support, together with the first polarity electrode needles 11, can be attached to and detached from the main body of the electrode.

Electro-Conductive Portion for the First Polarity

The members constituting the electrode needle holding portion 10 include the electro-conductive portion 14 for the first polarity. The electro-conductive portion 14 for the first polarity is a member provided at the upper side and/or inner side of the lower structural body 12 of the outer frame support and connected to the first polarity electrode needles 11 that penetrate the base portion of the lower structural body 12 of the outer frame support. That is, in the structure related to the first polarity electrode in the present invention, the first polarity electrode needles 11 penetrate the lower structural body 12 of the outer frame support of the electrode needle holding portion and are connected to the electro-conductive portion 14 for the first polarity. With its position and shape, the electro-conductive portion 14 for the first polarity is provided so as to be electrically isolated from the members related to the second polarity.

The electro-conductive portion 14 for the first polarity can supply voltage to the first polarity electrode needles 11 when it is connected to the power supply through wiring.

The electro-conductive portion 14 for the first polarity can have any shapes connectable to the electrode needles of the first polarity electrode needles 11 and capable of supplying electric power to the electrodes. Examples of the shape of the electro-conductive portion 14 for the first polarity are a flat planar shape and a substantially flat planar shape having a certain thickness. More specific examples are those having circular or substantially circular cross sections.

The electro-conductive portion 14 for the first polarity has a shape provided with a connecting portion/connecting portions 16 with the first polarity electrode needles 11. A shape provided with a connecting portion/connecting portions 16 to be connected with all the electrode needles of the first polarity electrode needles 11 is preferable. The electro-conductive portion 14 for the first polarity can be connected with and fixed to the first polarity electrode needles 11 by welding, for example, and it is also possible to employ a detachably connectable structure.

The electro-conductive portion 14 for the first polarity preferably has a shape to avoid direct contact with the path for syringe needle insertion and removal 40. For example, when the electro-conductive portion 14 for the first polarity has a flat planar shape or the like, it preferably has an opening portion 15 to avoid contact with the path for syringe needle insertion and removal 40. When the electro-conductive portion for the first polarity is not provided with the opening portion 15, it preferably has an annular shape, a substantially annular shape or a polygonal annular shape to avoid contact with the path for syringe needle insertion and removal 40. A C shape, an L shape or a shape similar to these shapes can also be adopted.

In some embodiments, a spacer portion 47 made of electrically insulating material can be provided between the electro-conductive portion 14 for the first polarity and the electro-conductive portion 42 for the second polarity to avoid contact between the electro-conductive portion 14 for the first polarity and the electro-conductive portion 42 for the second polarity. That is, it is possible to employ a structure in which the contact between the electro-conductive portion 14 for the first polarity and the electro-conductive portion 42 for the second polarity can be blocked by the spacer portion 47 made of electrically insulating material.

Further, when the path for syringe needle insertion and removal 40 has a disconnected portion and the syringe needle 52 is exposed in the vicinity of the opening portion 15, it is desirable to determine the size of the opening portion 15 so as to ensure a sufficient distance between the inner portion of the opening 15 and the syringe needle 52.

The electro-conductive portion 14 for the first polarity is preferably made of electro-conductive material. It can be made of any material that can be generally used as an electrode, and metallic material is preferable. Preferable examples are stainless steel, platinum, steel, copper, iron, titanium alloy, aluminum alloy and carbon. Such materials as stainless steel, platinum, and titanium alloy, which are resistant to rust and whose impact on the body is not concerned, are especially preferable.

In some embodiments, the electro-conductive portion 14 for the first polarity can be provided as a member integrated with wiring, conducting wires and/or power cables.

In the present invention, it is possible to employ a cartridge-type electrode in which the first polarity electrode needles, together with a part of or the entire lower structural body 12 of the outer frame support, can be attached and detached. In an embodiment of this cartridge electrode, the first polarity electrode needles 11 can be attached and detached at the connecting portion 16 between the first polarity electrode needles and the electro-conductive portion 14 for the first polarity. That is, the first polarity electrode needles 11 can be provided as a structure that can be detachably attached by means of the connecting portion 16 with the electro-conductive portion for the first polarity.

Moreover, in one embodiment, the connecting portion 16 can be provided as a structure that allows the electro-conductive portion 14 for the first polarity to be detached. That is, in this embodiment, a structure in which the connecting portion 16 capable of detaching the electro-conductive portion 14 for the first polarity is provided can be employed.

In these embodiments, the first polarity electrode needles 11 can be attached and detached together with a part of or the entire lower structural body 12 of the outer frame support. The first polarity electrode needles 11 can be replaced like a cartridge, and the risks such as contamination can be further reduced.

[Structure Related to the Second Polarity]

In the electrode for electroporation 1 according to the present invention, the structure related to the second polarity includes the syringe holding portion 20 and the like. In addition, the structure related to the second polarity may include wiring, conducting wires and/or power cables for connecting to the power source, and supporting members for reinforcing the outer frame support.

[Syringe Holding Portion]

In the electrode for electroporation according to the present invention, the syringe holding portion 20 for inserting a syringe needle 52 and mounting a syringe is provided on a side opposite to the electroporation target side of the electrode needle holding portion.

The electrode for electroporation 1 according to the present invention has the syringe holding portion 20 for physically supporting the syringe 50 and supplying voltage to the syringe needle 52, which serves as the second polarity electrode needle. The syringe holding portion 20 is a member for inserting the syringe needle 52 from the side opposing to the bottom surface of the lower structural body 12 of the outer frame support of the electrode needle holding portion and physically mounting and fixing the syringe. With the structure of the syringe holding portion 20 in the present invention, the syringe 50 can be supported physically, and at the same time, the syringe needle 52 can function as the second polarity electrode needle.

Here, the syringe holding portion 20 has, as its component members, the syringe barrel end attachment portion 21, the path for syringe needle insertion and removal 40, and the electro-conductive portion 42 for the second polarity as described below. Also, the syringe holding portion 20 can be provided with a spacer portion 47 depending on the requirements of particular embodiments.

Syringe Barrel End Attachment Portion

The members constituting the syringe holding portion 20 include the syringe barrel end attachment portion 21 for supporting the main body of the syringe.

The syringe barrel end attachment portion 21 is a member for attaching the syringe barrel end and supporting the main body of the syringe. Therefore, with regard to the shape of the syringe barrel end attachment portion 21, it is preferable that the outer frame can physically support the syringe as the outer frame support, and that the inner portion is hollowed. The upper portion of the syringe barrel end attachment portion preferably has an opening 27 suitable for mounting the syringe. More preferably, the syringe barrel end attachment portion has a cylindrical shape.

To further improve the functions of the syringe barrel end attachment portion 21, the syringe barrel end attachment portion 21 can be a dual structure formed by combining the inner portion for mounting the syringe barrel end and the outer frame support at the outer portion. In this embodiment of the dual structure, the syringe barrel end attachment portion 21 is composed of the inner portion of the syringe barrel end attachment portion, which is an inner structural body 24, and the outer portion of the syringe barrel end attachment portion, which is an outer structural body 22 (upper structural body of the outer frame support).

With regard to the size of the inner structural body 24 of the syringe barrel end attachment portion, a shape having an inner space 25 suitable for directly attaching and fixing the barrel end is desirable. The inner space 25 preferably has a size fitting the outer diameter of the syringe. The upper portion of the inner structural body 24 preferably has an open cylindrical shape.

With regard to the size of the inner structural body 24 of the syringe barrel end attachment portion, examples of its inner diameter or inner width when viewed from the top are 2 to 40 mm, preferably 3 to 20 mm, and more preferably about 4 to 15 mm.

Examples of the vertical height of the inner structural body 24 are 2 mm or more, preferably 3 mm or more, and more preferably 5 mm or more. The upper limit is not particularly limited, and it can be 50 mm or less, and preferably 20 mm or less, for example.

The inner structural body 24 of the syringe barrel end attachment portion can be made of any material having enough strength to support the syringe. It can be made of electrically insulating material. For example, it is preferably made of such material as that of the lower structural body 12 of the outer frame support as mentioned above. The material of the inner structural body 24 of the syringe barrel end attachment portion can be provided as a member connected to or continuous to the path for syringe needle insertion and removal 40. In this case, the inner structural body is preferably made of electro-conductive material, just like the material of the electro-conductive portion 42 for the second polarity of the path for syringe needle insertion and removal as described below.

When the inner structural body 24 of the syringe barrel end attachment portion is provided as an electro-conductive member connected to or continuous to the electro-conductive portion 42 for the second polarity, the inner structural body 24 of the syringe barrel end attachment portion can be provided with wirings and the like. In one such embodiment, the inner structural body can a member integrated with wiring, conducting wires and/or power cables.

Though the outer structural body 22 of the syringe barrel end attachment portion can be made of any material having enough strength as a housing, electrically insulating material is preferable from the viewpoint of safety.

When the outer structural body 22 and/or the inner structural body 24 of the syringe barrel end attachment portion are made of electrically insulating material, the insulating material preferably has hardness and durability, and for example, such material as that of the lower structural body 12 of the outer frame support as mentioned above is preferable.

The syringe barrel end attachment portion 21 is a member continuous to and/or connected to the upper portion of the lower structural body 12 of the outer frame support of the electrode needle holding portion 10. The outer structural body 22 of the syringe barrel end attachment portion and the lower structural body 12 of the outer frame support can be provided as an integrated member depending on the requirements of particular embodiments.

The inner structural body 24 of the syringe barrel end attachment portion is a structure continuous to, adjacent to, and/or connected to the hole for syringe needle insertion and removal 45, which is the upper end of the path for syringe needle insertion and removal 40. The inner structural body 24 of the syringe barrel end attachment portion and the path for syringe needle insertion and removal 40 can be provided as an integrated member depending on the requirements of particular embodiments.

Path for Syringe Needle Insertion and Removal

The electrode for electroporation 1 according to the present invention has the path for syringe needle insertion and removal 40 through which the inner structural body 24 of the syringe barrel end attachment portion and the lower structural body 12 of the outer frame support of the electrode needle holding portion communicate with or intermittently communicate with each other.

The path for syringe needle insertion and removal 40 preferably has a tubular structure or a discontinuous tubular structure through which the syringe needle 52 can be inserted or removed when the syringe is attached to the syringe barrel end attachment portion 21.

Specifically, the path for syringe needle insertion and removal 40 is preferably a straight-tubular path having an inner diameter or an inner width that allows to securely fix the syringe needle 52 when it is fully inserted and that allows smooth insertion and removal of the needle. More preferably, the path for syringe needle insertion and removal has a tubular shape whose cross section is circular. Even a structure which has spaces on the tube wall of the path or a discontinuously communicated structure in which the tube wall is not continuous can also be employed as the path for syringe needle insertion and removal if there is no risk of electric leakage or the like.

Here, the terms "discontinuously communicated" and "discontinuous" indicate that, though the path for syringe needle insertion and removal 40 is divided into two or more parts, these parts of the path are arranged in a line, and the insertion and removal of the syringe needle 52 are not practically affected.

The entire path for syringe needle insertion and removal 40 can be of any length which allows the portion of the syringe inserted and projecting from the hole for syringe needle insertion and removal 46 of the lower structural body 12 of the outer frame support of the electrode needle holding portion to have a needle length that can secure an appropriate distance and position with respect to the first polarity electrode needles 11.

In the electrode for electroporation 1 according to the present invention, the syringe holding portion 20 has the electro-conductive portion 42 for the second polarity made of electro-conductive material.

Preferably, the syringe holding portion 20 has the path for syringe needle insertion and removal 40 having, on at least a part thereof, the electro-conductive portion 42 for the second polarity made of electro-conductive material.

Here, the electro-conductive portion 42 for the second polarity is a member designed to have a portion to be brought into contact with the syringe needle 52 when a syringe is attached. By being connected to the power supply through wiring and the like, the electro-conductive portion for the second polarity can supply voltage to the syringe needle, which serves as the second polarity electrode needle.

The electro-conductive portion 42 for the second polarity is preferably made of electro-conductive material. It can be made of any material that can be generally used as an electrode. Preferable examples are stainless steel, platinum, steel, copper, iron, titanium alloy, aluminum alloy and carbon. Such materials as stainless steel, platinum, and titanium alloy, which are resistant to rust and whose impact on the body is not concerned, are especially preferable.

In some embodiments, the electro-conductive portion 42 for the second polarity can be provided as a member integrated with wiring, conducting wires and/or power cables.

With regard to the shape of the electro-conductive portion 42 for the second polarity, at least a portion of the electro-conductive portion 42 for the second polarity in the path for syringe needle insertion and removal has a straight-tubular structure made of electro-conductive material and has an inner diameter or an inner width that ensures contact with the syringe needle 52 inserted.

The electro-conductive portion 42 for the second polarity can have any shape that can realize electrical connection with the syringe needle 52 when the syringe is attached. Specifically, the electro-conductive portion for the second polarity preferably has a fine path structure allowing the insertion of the syringe needle, so that the contact with the syringe needle 52 can be ensured.

This configuration can be realized by forming the aforementioned portion of the path for syringe needle insertion and removal 40 by electro-conductive material. The path for syringe needle insertion and removal 40 can also function as the electro-conductive portion 42 for the second polarity by forming, covering or coating the inner portion of the path for syringe needle insertion and removal 40 with electro-conductive material.

The electro-conductive portion 42 for the second polarity of the path for syringe needle insertion and removal is preferably a straight-tubular path for insertion and removal having an inner diameter or an inner width that secures the contact with the syringe needle when the needle is fully inserted and that allows smooth insertion and removal of the needle. Specific examples of the inner diameter or the inner width at the narrowest portion are 0.1 to 1 mm, preferably 0.2 to 0.8 mm, more preferably 0.3 to 0.7 mm, and even more preferably 0.35 to 0.6 mm. Moreover, the inner diameter or the inner width at the narrowest portion is larger than the outer diameter of the syringe needle by 0.01 to 1 mm, preferably 0.05 to 0.5 mm, more preferably 0.07 to 0.4 mm, and even more preferably about 0.1 to 0.3 mm to secure the contact between the syringe needle and the electro-conductive portion for the second polarity and to realize the smooth insertion and removal of the needle.

The electro-conductive portion 42 for the second polarity preferably has a path length that can secure the contact with the syringe needle, when the needle is fully inserted, and the smooth insertion and removal of the needle. Examples of the path length are 0.1 to 10 mm, preferably 0.25 to 7.5 mm, and more preferably 0.5 to 5 mm from the viewpoint of securing contact with the syringe needle.

With regard to the position of the electro-conductive portion 42 for the second polarity in the path for syringe needle insertion and removal 40, while the electro-conductive portion 42 for the second polarity can be formed at the central portion and/or the lower portion of the path for syringe needle insertion and removal 40, it is preferably formed at a position including the upper portion, which is the syringe barrel end attachment portion side, of the path for syringe needle insertion and removal.

Especially, when the inner structural body 24 of the syringe barrel end attachment portion is made of electro-conductive material, the electro-conductive portion 42 for the second polarity preferably has a shape continuous to or connected to the bottom portion 26 of the inner structural body of the syringe barrel end attachment portion. In one such embodiment, the syringe barrel end attachment portion 21 can be provided being connected to wiring, conducting wires and/or power cables.

With regard to the shape of the path for syringe needle insertion and removal at the portion around the electro-conductive portion 42 for the second polarity, the diameter at the upper portion, from which the syringe needle 52 is inserted, can be slightly large, and the diameter can be narrowed gradually along the path for insertion and removal. Such configuration is preferable, because the syringe needle 52 can be inserted easily and smoothly and can certainly be brought into electrical contact with the electro-conductive portion for the second polarity.

The portion of the path for syringe needle insertion and removal 40 at the lower structural body side of the outer frame support is a path for insertion and removal 44 made of electrically insulating material. The lower structural body 12 of the outer frame support of the electrode needle holding portion is a member having the hole for syringe needle insertion and removal 46 in its bottom surface.

Said path for insertion and removal made of electrically insulating material can have such an inner diameter or an inner width as that of the hole for syringe needle insertion and removal 46 of the lower structural body of the outer frame support. An inner diameter or an inner width that ensures smooth insertion and removal of the syringe needle 52 is preferable for the path for insertion and removal made of electrically insulating material.

The length of the path for insertion and removal made of electrically insulating material is equivalent to the thickness of the lower structural body 12 of the outer frame support. The path for insertion and removal made of electrically insulating material can be of any length if the portion of the syringe needle projecting from the bottom surface of the lower structural body 12 of the outer frame support can have a predetermined length.

A part of the path for syringe needle insertion and removal 40 can be formed by a spacer member 47 which is made of electrically insulating material and provided as a separate member. For example, a tubular structure or the like formed as a spacer member can be provided as a part of the path for syringe needle insertion and removal 40 connecting the lower structural body 12 of the outer frame support and the electro-conductive portion 42 for the second polarity.

Even a structure which has spaces on the tube wall of the path or has a discontinuously communicated structure in which the tube wall is not continuous can also be employed as the path for syringe needle insertion and removal 40 if safety can be assured.

Spacer Portion

The electrode for electroporation 1 according to the present invention can have a desired spacer portion 47 depending on the requirements of particular embodiments.

The spacer portion 47 is provided for various purposes, such as physically supporting or protecting the arrangement and composition of the electro-conductive members, and especially, it is provided to avoid direct contact between the electro-conductive members related to the first polarity and the members related to the second polarity.

The spacer portion 47 is preferably made of electrically insulating material. Material having hardness and durability can be employed as the electrically insulating material, and for example, such material as that of the lower structural body 12 of the outer frame support as mentioned above is preferable.

In one embodiment of the spacer portion 47, a part of the path for syringe needle insertion and removal 40 can be formed by the spacer portion 47. In this case, direct contact between the electro-conductive portion 42 for the second polarity of the path for syringe needle insertion and removal 40 and the electro-conductive portion 14 for the first polarity of the lower structural body of the outer frame support can be avoided.

In another embodiment, when the inner structural body 24 of the syringe barrel end attachment portion is made of an electro-conductive member, a member which is, for example, hollowed in a funnel shape or an inverted cone shape can be sandwiched as the spacer portion to avoid the contact between the inner structural body 24 of the syringe barrel end attachment portion and the electro-conductive portion 14 for the first polarity.

2. Embodiments with Syringe Attached

The electrode for electroporation 1 according to the present invention serves as an electrode member in which, when a syringe is attached to the syringe holding portion 20 and the syringe needle is brought into contact with the electro-conductive portion for the second polarity, the syringe needle 52 projecting from the hole for syringe needle insertion and removal 46 can be used as the second polarity electrode needle 55.

Therefore, in the embodiment of the present invention with the syringe 50 attached, the electrode for electroporation has a structure in which the syringe needle projects from the hole for syringe needle insertion and removal, and the projecting syringe needle functions as the second polarity electrode needle.

[Attachment of the Syringe]

In the electrode according to the present invention, any existing or novel syringe of any size that can fit the structure and the like of the syringe holding portion can be attached and used. Especially, a syringe having a capacity of 0.5 to 50 mL, preferably 0.5 to 10 mL, and more preferably about 0.5 to 5 mL is preferable. A general cylinder and plunger made of resin such as polypropylene can be employed, but there is no limitation on their material.

In the electrode according to the present invention, the electrode for electroporation in which the syringe needle itself functions as the second polarity electrode needle can be obtained, as the syringe needle projecting from the hole for syringe needle insertion and removal is brought into contact with the electro-conductive portion for the second polarity. That is, the electrode according to the present invention can become the electrode for electroporation in which the syringe needle serves as the second polarity electrode needle when the syringe is attached to the syringe holding portion 20.

Here, the "second polarity electrode needle 55" as used herein refers to the syringe needle which serves as a needle electrode with polarity opposite to that of the voltage applied to the first polarity electrode needles 11.

The syringe needle according to the present invention is preferably made of electro-conductive material. It can be made of any material that can be generally used as an electrode, and metallic material is preferable. Preferable examples are stainless steel, titanium alloy and platinum.

The syringe needle can have any shape as long as it is a hollow needle shape, and an example thereof is a syringe needle shape. The syringe needle can have any outer diameter suitable for piercing into living tissue, and examples thereof are 0.08 mm (37 gauge) or more, preferably 0.1 mm (36 gauge) or more, more preferably 0.2 mm (34 gauge) or more, and even more preferably 0.26 mm (32 gauge) or more. The upper limit thereof is 0.4 mm (27 gauge) or less, for example.

The syringe needle can be of any length suitable for piercing into living tissue, and in the electrode according to the present invention, the syringe needle provided as the second polarity electrode needle preferably has a length within a predetermined range.

Specifically, the length of the projecting portion of the syringe needle, which serves as the second polarity electrode needle, from the hole for syringe needle insertion and removal preferably falls within a range of −4 to +2 mm, preferably −3 to +1 mm, more preferably −3 to ±0 mm, more preferably −2 to −0.5 mm, and even more preferably −1.5 to −0.5 mm compared with the average length of the portions of the first polarity electrode needles 11 projecting from the bottom surface of the lower structural body 12 of the outer frame support of the electrode needle holding portion. In the electrode according to the present invention, it is preferable to dispose the syringe needle so that the position of the tip of the syringe needle attached can be located within this range. As a consequence, electric pulses can be applied to the area into which foreign substances have been injected at several millimeters depth and at which the foreign substances are concentrated.

3. Product Forms

The electrode for electroporation 1 according to the present invention can be used to manufacture an electrode product for electroporation having a plurality of the first polarity electrode needles.

Specifically, it can be used to produce an electrode part in which, when a syringe is attached to the syringe holding portion 20, the syringe needle protruding from the hole for syringe needle insertion and removal 46 can be used as the second polarity electrode needle 55.

Also, it can be used to produce a product having a structure in which the syringe is attached to the syringe holding portion 20, the syringe needle projects from the hole for syringe needle insertion and removal 46, and the projecting syringe needle functions as the second polarity electrode needle 55.

In the present invention, a kit for assembling the electrode for electroporation including members of the first polarity electrode needles 11, the electrode needle holding portion 10 and the syringe holding portion 20 as described above can be produced. That is, in the present invention, an assembly kit in which these members can be assembled can be produced.

In the assembly kit according to the present invention, a product in which each of the first polarity electrode needles 11, the electrode needle holding portion 10 and the syringe holding portion 20 is provided as an independent component member can be produced. Also, in the assembly kit, two of the component members can be provided as a connected or integrated member. For example, in one such embodiment, the electrode needle holding portion 10 and the syringe holding portion 20 are provided being connected or integrated with each other, and the first polarity electrode needles 11 are provided separately.

In an embodiment of the assembly kit according to the present invention, a part of the component members can be provided separably. A part of the separated member/members can be provided being connected to or integrated with another member or members. In one such embodiment, a cartridge electrode described above can be provided.

In addition to the component members as described above, the assembly kit according to the present invention can include the syringe 50 as its component member.

Moreover, the assembly kit including the syringe can include the electrode member 1, to which the syringe is not attached and which is provided in an assembled state, and the syringe, which is provided as a separate member.

4. In Vivo Electroporation

The electrode for electroporation 1 with the syringe attached according to the present invention is especially preferable for in vivo electroporation. Especially, in the present invention, in vivo electroporation in muscle tissue or skin tissue, into which it has been difficult to stably introduce foreign substances, can be performed stably and at high efficiency.

In the present invention, by using the electrode for electroporation having a plurality of electrodes, a series of operations from the injection of a solution containing foreign substances to the application of voltage can be performed stably in a very short time.

Specifically, because of the structural features as described above, electrical connection can be achieved just by the insertion of the syringe needle. Therefore, the electrode for electroporation can be used without connecting the electrode using a hook or the like. Moreover, since the electrodes are fixed electrodes having predetermined lengths, direct injection into the muscle tissue or the like can be realized without requiring the adjustment of the needle depth. Further, electric pulses can be applied simultaneously with or immediately after the injection of the foreign substances from the syringe. These operations can be performed without requiring special skills.

In the present invention, since the sample can be installed just by attaching the syringe, a series of operations, including the preparatory operations from the assembly of the electrode device to the injection of the sample, can be performed quickly and easily, and the electrode device can be used stably and conveniently in research or medical treatment. Moreover, since the sample can be changed just by exchanging the syringe, the risk of contamination and infection can be reduced.

Further, the first polarity electrode needles 11 can be easily subjected to such sterilization procedures as ethanol sterilization and heat sterilization and can be exchanged when necessary.

The electrode according to the present invention is applicable to any electric pulse patterns. For example, they are applicable to electric pulses of attenuated waves, rectangular waves, attenuated rectangular waves and continuous waves. Moreover, it is expected that gene introduction efficiency will be improved further by using the electrode according to the present invention in combination with such a method as multiple-stage electroporation, in which poring pulses at high voltage and transfer pulses at low voltage are applied successively.

EXAMPLES

Hereinafter, the present invention will be explained by way of examples, but the scope of the invention is not limited thereto.

[Example 1] Electrode for Electroporation Having a Plurality of Electrode Needles An electrode for electroporation 1 as shown in FIGS. 1 to 13 was produced as an embodiment of the electrode according to the present invention. Hereinafter, the electrode for electroporation 1 produced in this example will be explained with reference to the exploded views, the component drawings and the like.

(1) Structure Related to the First Polarity

In the electrode for electroporation in this example, three hypodermic needles (0.26 mm diameter, 8.5 mm length) made of stainless steel, which were provided as the first polarity electrode needles 11, were welded and fixed to the electro-conductive portion 14 for the first polarity. The first polarity electrode needles 11 are fixed electrode needles which are inserted and fixed to the electrode through holes 13 formed in the bottom surface of the lower structural body 12 of the outer frame support, which serves as the housing, so that the first polarity electrode needles may be perpendicular to the bottom surface.

The electro-conductive portion 14 for the first polarity is a substantially circular flat plate member made of stainless steel having a thickness of about 1.5 mm, whose connecting portions 16 with the members of the first polarity electrode needles 11 have recessed shapes. The electro-conductive portion 14 for the first polarity is connected to the power source by wiring. An opening 15 is provided at a central portion of the electro-conductive portion 14 for the first polarity in order to establish the communication of the path for syringe needle insertion and removal 40.

The lower structural body 12 of the outer frame support is a member forming the main body of the outer frame of the electrode of this example and is made of polycarbonate resin, which is electrically insulating material. The outer diameter of the lower structural body 12 of the outer frame support is 10 mm when viewed from the bottom.

In the electrode for electroporation 1 in this example, the length of the portion of the first polarity electrode needles 11 protruding from the bottom surface of the lower structural body 12 of the outer frame support is fixed to 5 mm when measured from the bottom surface of the lower structural body of the outer frame support. The first polarity electrode needles 11 are arranged on a circle at equal intervals when viewed from the bottom of the lower structural body 12 of the outer frame support. Specifically, the first polarity electrode needles 11 are arranged on a circle of 1.5 mm radius (3 mm diameter) whose center is located at the center of the hole for syringe needle insertion and removal 46.

(2) Structure Related to the Second Polarity

In the electrode in this example, the portion above the lower structural body 12 of the outer frame support serves as a member forming the outer structural body 22 of the syringe barrel end attachment portion, which has a substantially cylindrical shape with an outer diameter of 10 mm. The inner structure thereof has a substantially cylindrical hollow with an inner diameter of 6 mm.

The inner structural body 24 of the syringe barrel end attachment portion is buried and maintained inside the outer structural body of the syringe barrel end attachment portion (22: upper structural body of the outer frame support). The inner structural body 24 of the syringe barrel end attachment portion is a member made of stainless steel and has a substantially cylindrical hollow with an inner diameter of 4.4 mm and a height of 5.35 mm, and the portion below this hollow is provided with a narrower, substantially cylindrical hollow with an inner diameter of 3.2 mm and a height of 1 mm. The hole for syringe needle insertion and removal 45 is formed at the center of the bottom surface of the inner structure 25. The inner structural body 24 of the syringe barrel end attachment portion is a member connected to the power source by wiring.

The lower part of the inner structural body 24 of the syringe barrel end attachment portion is connected and fixed to the lower structural body 12 of the outer frame support, with the spacer portion 47, which serves as the collar, being sandwiched between them. The spacer portion 47 is a member made of polycarbonate, which is electrically insulating material, and functions as an insulating member for avoiding direct contact between the electro-conductive portion 14 for the first polarity and the region electrically connected to the second polarity electrode.

The electrode in this example has a structure in which the inner structural body 24 of the syringe barrel end attachment portion and the lower structural body 12 of the outer frame support communicate with each other, forming the path for syringe needle insertion and removal 40, which is a tubular channel structure.

The path for syringe needle insertion and removal 40 is formed to be extending from the hole for syringe needle insertion and removal 45 in the bottom portion 26 of the inner structural body of the syringe barrel end attachment portion toward the lower structural body 12 of the outer frame support. The path for syringe needle insertion and removal 40 forms the electro-conductive portion 42 for the second polarity, which is a straight-tubular path with a length of 1.6 mm and a cross sectional diameter of 0.5 mm. The electro-conductive portion for the second polarity secures the contact with the syringe needle, and as a result, electricity can be supplied to the syringe needle.

The spacer portion 47 has a tubular structure 43 around the outer side of the straight tubular path of the electro-conductive portion 42 for the second polarity to protect the outer wall of the electro-conductive portion for the second polarity, and the contact between the electro-conductive portion for the second polarity and the electro-conductive portion 14 for the first polarity is avoided. The path for insertion and removal 44 formed by the base material of the lower structural body 12 of the outer frame support is provided at the lower part of the path for syringe needle insertion and removal 40, and the hole for syringe needle insertion and removal 46 with a diameter of 1 mm is formed in the bottom surface of the lower structural body of the outer frame support.

(3) Product Forms

Figure 11:
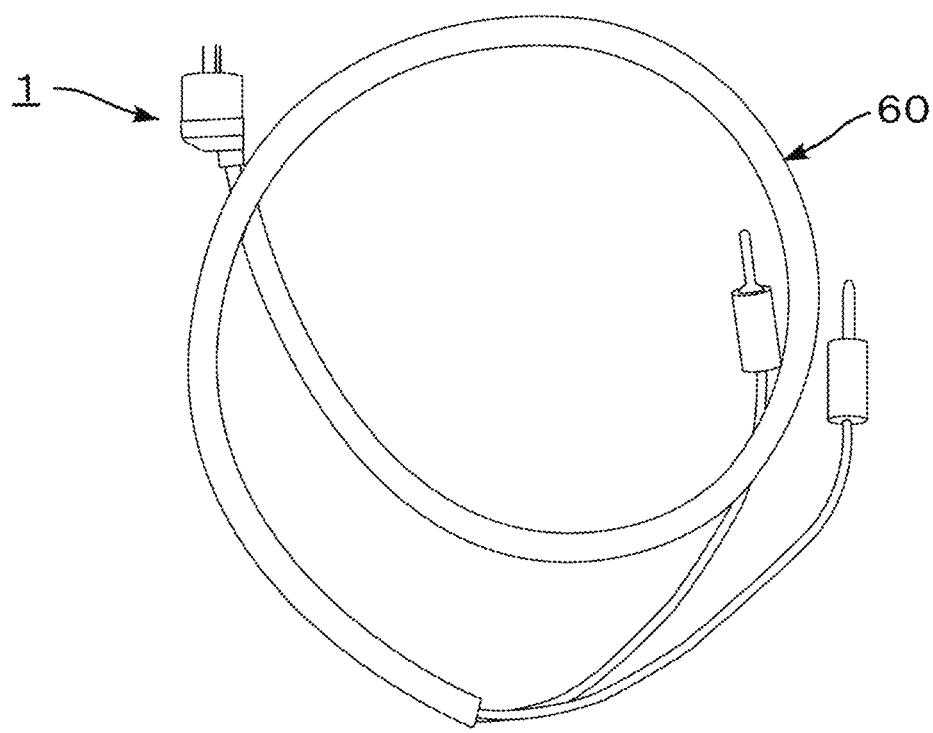
FIG. 11 is a photographic image of the entire electrode for electroporation according to one example of the present invention.
Figure 12A:
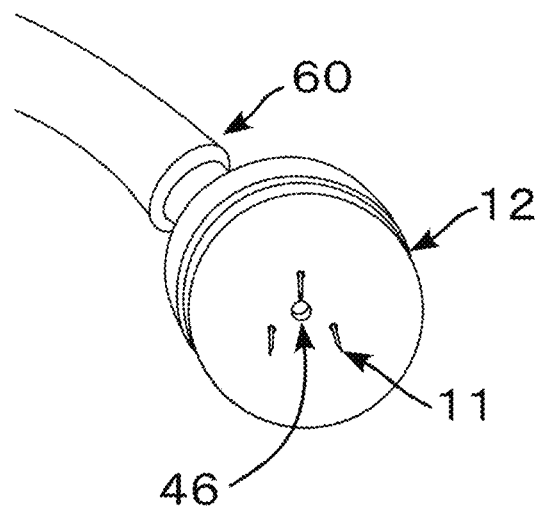
FIGS. 12A and 12B show photographic images of the electrode for electroporation according to one example of the present invention.
Figure 12B:
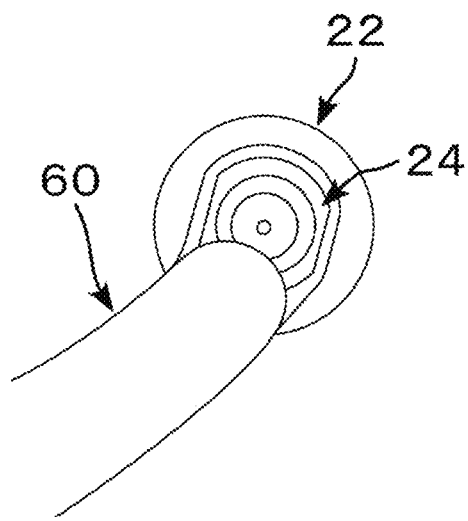
Figure 13A:
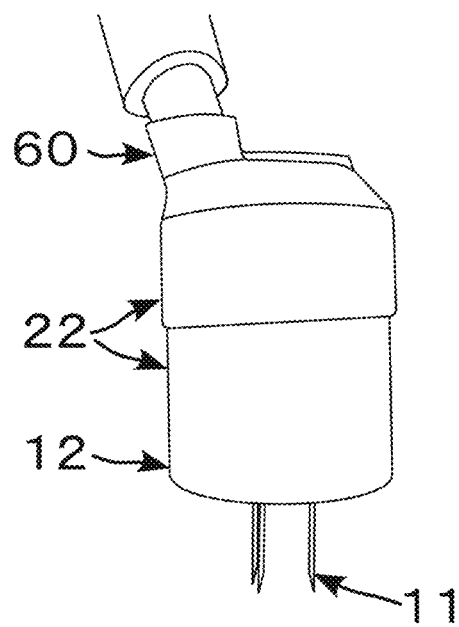
FIGS. 13A and 13B show photographic images of the electrode for electroporation according one example of the present invention.

FIGS. 11 to 13 show the photographic images of the electrode for electroporation having a plurality of electrodes produced in this example. In the electrode for electroporation, the positive or negative voltage can be applied to either of the first polarity electrodes or the second polarity electrode.

[Example 2] Electrode for Electroporation with Syringe Attached

An electrode for electroporation in which a commercially available syringe was attached to the electrode produced in the example above was assembled and produced.

(1) Attachment of the Syringe

The syringe needle 52, which is the tip portion of the syringe 50, was fully inserted to the hole for syringe needle insertion and removal 45 in the bottom portion 26 of the inner structural body of the syringe barrel end attachment portion of the electrode for electroporation having a plurality of the first polarity electrode needles produced in Example 1, and the tip portion of the syringe needle was protruded from the hole for syringe needle insertion and removal 46 in the bottom surface of the lower structural body of the outer frame support. This way, the electrode for electroporation 1 having the first polarity electrode needles and the syringe needle, which became the second polarity electrode needle, was assembled.

A 0.5 mL insulin syringe (Myjector (registered trademark), Terumo Corporation) was used as the syringe 50 attached. A 29-gauge syringe needle 52 (0.33 mm diameter, 13 mm needle length) was used.

Figure 13B:
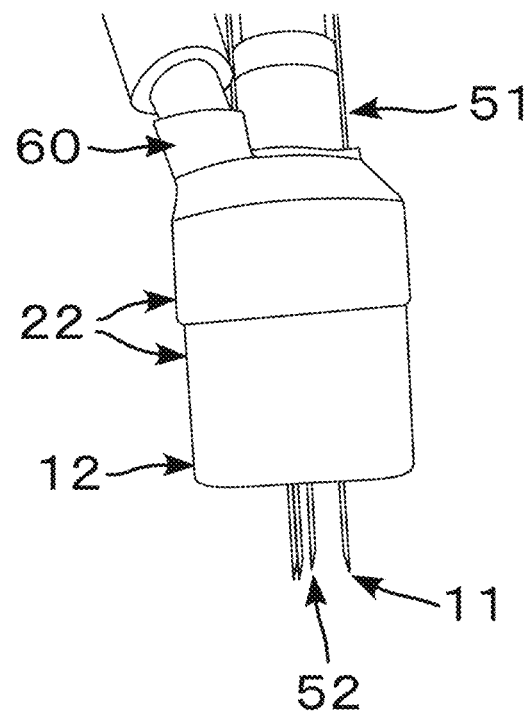
Figure 14A:
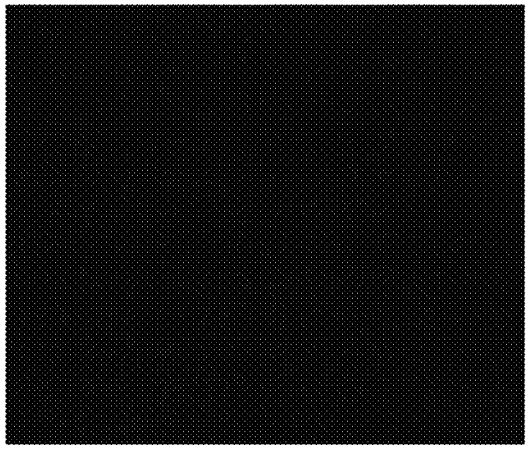
FIGS. 14A, 14B, 14C, 14D and 14E show photographic images indicating the expression of the green fluorescent protein detected in the gene introduction into the mouse thigh muscle in Example 3. The bright areas in the photographs indicate the expression of the GFP.
Figure 14B:
Figure 14C:
Figure 14D:
Figure 14E:
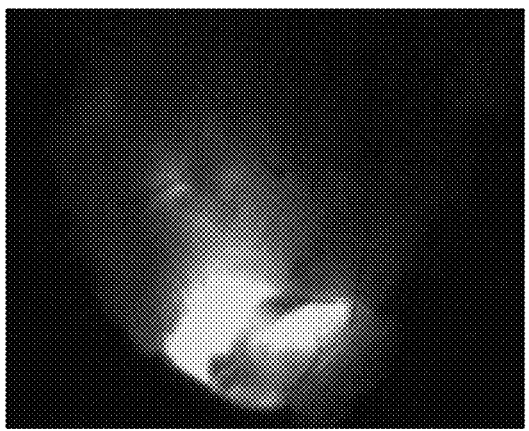

In the electrode with the syringe attached in this example, the length of the portion of the syringe needle 52, or the second polarity electrode needle, protruding from the hole for syringe needle insertion and removal 46 in the lower structural body 12 of the outer frame support was fixed to 4 mm when measured from the bottom surface of the lower structural body 12 of the outer frame support. That is, the tip of the syringe needle was located at a position 1 mm lower than the tips of the first polarity electrode needles 11, whose length was fixed to 5 mm (2) Product Forms FIG. 13B shows a photographic image of the electrode with the syringe attached produced in this example. The attachment of the syringe can be completed only by the simple assembly operation of inserting the syringe needle. In the electrode for electroporation, the positive or negative voltage can be applied to either of the first polarity electrodes or the second polarity electrode.

[Example 3] Gene Introduction into Muscle Tissue

Gene introduction into muscle tissue was performed using the electrode for electroporation having electrode needles produced in the example above.

All the hair of the thigh of anaesthetized mice was removed with a depilatory agent, and the remaining depilatory agent was wiped thoroughly with 70% ethanol. As the preparatory treatment, the thigh muscle was injected with hyaluronidase (40 U/mL) three times (20 µL each time) and left for 30 minutes. Then, electroporation was performed by injecting a DNA solution and applying electric pulses using the electrode for electroporation produced in Example 2. More specifically, solutions containing 0.5 to 1.5 µg/µL phMGFP were prepared as the DNA solution and filled into the syringe. The electrode for electroporation described in Example 2 was assembled, and the solution was injected at amounts shown in Table 1. A solution not containing DNA was prepared as a control (Experiment 3-1) and the same procedures were performed. NEPA 21 (Nepa Gene Co., Ltd.) was used as the electroporator. The electric pulses as shown in Table 2 were applied. The fluorescence of GFP was observed five days after the electroporation. FIG. 14 shows the fluorescent microscopy images.

The results show that the electroporation using the electrode produced in the example above can realize effective gene introduction with simple operations even in the skeletal muscle, in which conventional techniques could only achieve low gene introduction efficiency. Moreover, with this electrode, a series of operations could be performed quickly, as the first polarity electrode needles and the second polarity electrode needle could be inserted into the tissue simultaneously and the adjustment of the insertion depth was not required. Practically, with the structural features of the electrode, the injection of the sample and the application of voltage could be performed simultaneously.

These results prove that the electrode for electroporation according to the present invention dramatically improve the operability in in vivo electroporation and can realize effective gene introduction even in the skeletal muscle, in which gene introduction efficiency tended to be low. Moreover, since the syringe attached was a disposable syringe, the sample could be easily installed, and electroporation could be performed with a reduced risk of contamination or infection.

TABLE 2

|  |  | Experiment 3-1 (FIG. 14A) | Experiment 3-2 (FIG. 14B) | Experiment 3-3 (FIG. 14C) | Experiment 3-4 (FIG. 14D) | Experiment 3-5 (FIG. 14E) |
| --- | --- | --- | --- | --- | --- | --- |
|  | Amount of DNA injected | 0 µg | 25 µg | 50 µg | 75 µg | 100 µg |
| Poring pulse | Voltage (V) | 35 | 35 | 35 | 35 | 35 |
|  | Pulse width (ms) | 30 | 30 | 30 | 30 | 30 |
|  | Pulse interval (ms) | 50 | 50 | 50 | 50 | 50 |
|  | Number of times | 3 | 3 | 3 | 3 | 3 |
|  | Attenuation rate (%) | 10 | 10 | 10 | 10 | 10 |
|  | Polarity | + | + | + | + | + |
| Transfer pulse 1 | Voltage (V) | 10 | 10 | 10 | 10 | 10 |
|  | Pulse width (ms) | 50 | 50 | 50 | 50 | 50 |
|  | Pulse interval (ms) | 50 | 50 | 50 | 50 | 50 |
|  | Number of times | 3 | 3 | 3 | 3 | 3 |
|  | Attenuation rate (%) | 40 | 40 | 40 | 40 | 40 |
|  | Polarity | + | + | + | + | + |
| Transfer pulse 2 | Voltage (V) |  | 10 | 10 | 10 | 10 |
|  | Pulse width (ms) | 50 | 50 | 50 | 50 | 50 |
|  | Pulse interval (ms) | 50 | 50 | 50 | 50 | 50 |
|  | Number of times | 3 | 3 | 3 | 3 | 3 |
|  | Attenuation rate (%) | 40 | 40 | 40 | 40 | 40 |
|  | Polarity | − | − | − | − | − |

INDUSTRIAL APPLICABILITY

The present invention is expected to be applied in such fields as life science, including molecular biology, genetic engineering and cell biology, the medical field, including medical care and drug discovery, and animal husbandry, including livestock and poultry farming. Especially, it is expected to be effectively applied in technical fields utilizing in vivo electroporation.

LIST OF REFERENCE NUMERALS

1: Electrode for electroporation
10: Electrode needle holding portion
11: First polarity electrode needles
12: Lower structural body of the outer frame support
13: First polarity electrode through holes
14: Electro-conductive portion for the first polarity
15: Opening portion
16: Connecting portion
17: Wiring, cable
18: Wiring holding portion
20: Syringe holding portion
21: Syringe barrel end attachment portion
22: Outer structural body of the syringe barrel end attachment portion (upper structural body of the outer frame support)
23: Space inside the outer structural body of the syringe barrel end attachment portion
24: Inner structural body of the syringe barrel end attachment portion
25: Space inside the inner structural body of the syringe barrel end attachment portion
26: Bottom portion of the inner structural body of the syringe barrel end attachment portion
27: Opening portion
28: Wiring, cable
29: Wiring holding portion
40: Path for syringe needle insertion and removal
41: Path for syringe needle insertion and removal (in the syringe barrel end attachment portion)
42: Electro-conductive portion for the second polarity
43: Path for syringe needle insertion and removal (in the spacer portion)
44: Path for syringe needle insertion and removal (in the lower structural body of the outer frame support)
45: Hole for syringe needle insertion and removal (in the syringe barrel end attachment portion)
46: Hole for syringe needle insertion and removal (in the lower structural body of the outer frame support)
47: Spacer portion
50: Syringe, the entire syringe
51: Syringe barrel end
52: Syringe needle
53: Syringe barrel
54: Plunger
55: Second polarity electrode needle
60: Power cable

The invention claimed is:

1. An electrode for electroporation comprising a plurality of electrode needles, an electrode needle holding portion, and a syringe holding portion,
    wherein (A) said plurality of electrode needles consist of first polarity electrode needles;
    (B) the electrode needle holding portion is a structural body comprising a lower structural body of an outer frame support and an electro-conductive portion for a first polarity, a bottom surface of the lower structural body of the outer frame support being provided with a hole for syringe needle insertion and removal communicating with a syringe holding portion side;

(C) three or more first polarity electrode needles project from the bottom surface of the lower structural body of the outer frame support toward an electroporation target side, the hole for syringe needle insertion and removal being disposed inside a polygon whose apexes are tips of the first polarity electrode needles when viewed from a bottom of the lower structural body of the outer frame support;

(D) (d-1) the syringe holding portion for mounting a syringe having a syringe needle by inserting the syringe needle is provided on a side opposite to the electroporation target side of the electrode needle holding portion, the syringe holding portion comprising a syringe barrel end attachment portion, a path for syringe needle insertion and removal, and an electro-conductive portion for a second polarity, (d-2) the syringe barrel end attachment portion has a structure in which an inner structural body of the syringe barrel end attachment portion is buried and maintained inside an upper structural body of the outer frame support, the inner structural body of the syringe barrel end attachment portion comprising an inner space, which is suitable for attaching and fixing a syringe barrel end and whose upper portion has an opening, and a bottom portion, the inner space of the inner structural body of the syringe barrel end attachment portion having an inner diameter that can fit an outer diameter of the syringe;

(d-3) at least a portion of the path for syringe needle insertion and removal of the syringe holding portion is provided with the electro-conductive portion for the second polarity made of electro-conductive material, the path for syringe needle insertion and removal being a path through which the bottom portion of the inner structural body of the syringe barrel end attachment portion and the hole for syringe needle insertion and removal in the bottom surface of the lower structural body of the outer frame support of the electrode needle holding portion communicate with or intermittently communicate with each other, at least a portion of the electro-conductive portion for the second polarity in the path for syringe needle insertion and removal has a straight-tubular structure made of electro-conductive material and has an inner diameter or an inner width that ensures contact with the syringe needle inserted and that allows smooth insertion and removal of the syringe needle; and (E) the electrode for electroporation is an electrode member in which, when the syringe having the syringe needle is attached to the syringe holding portion by inserting the syringe needle into the path for syringe needle insertion and removal, the syringe is fixed, the syringe needle is brought into contact with the electro-conductive portion for the second polarity, and the syringe needle projecting from the hole for syringe needle insertion and removal can be used as a second polarity electrode needle.

2. The electrode for electroporation according to claim 1, wherein the first polarity electrode needles penetrate the lower structural body of the outer frame support of the electrode needle holding portion and are connected to the electro-conductive portion for the first polarity.

3. The electrode for electroporation according to claim 1, wherein angles at which the first polarity electrode needles project are perpendicular to and/or substantially perpendicular to the bottom surface of the lower structural body of the outer frame support.

4. The electrode for electroporation according to claim 1, wherein the first polarity electrode needles are located within a range of 0.5 to 10 mm from a center of the hole for syringe needle insertion and removal when viewed from the bottom of the lower structural body of the outer frame support.

5. The electrode for electroporation according to claim 1, wherein the first polarity electrode needles are arranged at equal intervals or substantially equal intervals on concentric circles or substantially concentric circles around the hole for syringe needle insertion and removal when viewed from the bottom of the lower structural body of the outer frame support.

6. The electrode for electroporation according to claim 1, wherein the first polarity electrode needles are fixed electrode needles, and a length of their portion projecting from the bottom surface of the outer frame support of the electrode needle holding portion is within a range of 1 to 10 mm.

\* \* \* \* \*